(12) United States Patent
Berleth et al.

(10) Patent No.: US 6,197,744 B1
(45) Date of Patent: Mar. 6, 2001

(54) TUMOR NECROSIS FACTOR INHIBITORY PROTEIN TIP $B_1$ AND METHOD OF USING SAME

(75) Inventors: Erica Berleth, North Tonawanda; M. Jane Ehrke, Lancaster; Srikanth S. Nadadur, Williamsville; Hira Gurtoo, East Amherst; Alicia Henn; Enrico Mihich, both of Buffalo, all of NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 09/157,910

(22) Filed: Sep. 21, 1998

(51) Int. Cl.[7] ..................................... A61K 38/19
(52) U.S. Cl. ............................... 514/2; 530/351
(58) Field of Search .................... 530/350, 351; 435/7.2

(56) References Cited

U.S. PATENT DOCUMENTS 5,136,021 * 8/1992 Dembinski et al. ................. 530/350

FOREIGN PATENT DOCUMENTS 0 308 378    9/1988 (EP) .

OTHER PUBLICATIONS

Wollman, E. et al., Cloning and Expression of a CDNA for Human Thioredoxin, the Journal of Biological Chemistry, vol. 263, No. 30, pp. 15506–15512 (1988).
Tagaya, Y. et al., ATL–Derived Factor (ADF), an IL–2 Receptor/TAc Inducer Homologous to Thioredoxin; Possible Involvement of Dithiol–Reduction in the IL–2 Receptor Induction; The EMBO Journal, vol. 8, No. 2, pp. 757–764 (1989).
Rajinder S. Sidhu et al., "Tumor Necrosis Factor Activities and Cancer Therapy–A Perspective," *Pharmacology & Therapeutics*, 1993, 57:79–128.
M.J. Ehrke et al., "Regulatory Role of Recombinant Human Tumor Necrosis Factor (rH–TNF) on Murine Control and Adriamycin–Modified Host Defense Functions," *XIVth Intl. Cancer Congress*, 3:916 (Abstract) 1986.
M. Jane Ehrke et al., "Species–Specific TNF Induction of Thymocyte Proliferation," *Cancer Immunol. Immunother.*, 1988, 27:103–108.
Kazuyoshi Hori et al., "Effect of Recombinant Human Tumor Necrosis Factor on the Induction of Murine Macrophage Tumoricidal Activity," *Cancer Research*, 1987, 47:2793–2798.
Kenneth F. Mace et al., "Role of Tumor Necrosis Factor in Macrophage Activation and Tumoricidal Activity," *Cancer Research*, 1988, 48:5427–5432.
Srdan Verstovsek et al., "Tumoricidal Activation of Murine Resident Peritoneal Macrophages by Interleukin 2 and Tumor Necrosis Factor α," *Cancer Research*, 1992, 52:3880–3885.
Peter Ujhazy et al., "TNF–α Potentiation of the Lymphokine–Activated Killer Response of Murine Thymus Cells," *Lymphokine and Cytokine Research*, 1994, 13, #2:99–106.
Christian M. Krawczyk et al., "Protective Specific Immunity Induced by Cyclophosphamide Plus Tumor Necrosis Factor α Combination Treatment of EL4–Lymphoma–Bearing C57BL/6Mice," *Cancer Immunol. Immunother.*, 1995, 40:347–357.
David Cosman, "A Family of Ligands of the TNF Receptor Superfamily," *Stem Cells*, 1994, 12:440–455.
Mike Rothe et al., "A Novel Family of Putative Signal Transducers Associated with the Cytoplasmic Domain of the 75 kDa Tumor Necrosis Factor Receptor," *Cell*, 1994, 78:681–692.
Hailing Hsu et al., "TRADD–TRAF2 and TRADD–FADD Interactions Define Two Distinct TNF Receptor 1 Signal Transduction Pathways," *Cell*, 1996, 84:299–308.
Louis A. Tartaglia et al., "The Two Different Receptors for Tumor Necrosis Factor Mediate Distinct Cellular Responses," *Proc. Natl. Acad. Sci.*, 1991, 88:9292–9296.
Louis A. Tartaglia et al., "A Novel Domain Within the 55 kd TNF Receptor Signals Cell Death," *Cell*, 1993, 74:845–853.
Laurie B. Owen–Schaub et al., "DNA Fragmentation and Cell Death is Selectively Triggered in Activated Human Lymphocytes by Fas Antigen Engagement," *Cellular Immunology*, 1992, 140:197–205.
Grace H. W. Wong et al., "Induction of Manganous Superoxide Dismutase by Tumor Necrosis Factor: Possible Protective Mechanism," *Science*, 1988, 242:941–944.
Sanjay Kumar et al., "Protection from Tumor Necrosis Factor–Mediated Cytolysis By Overexpression of Plasminogen Activator Inhibitor Type–2," *The Journal of Biological Chemistry*, 1991, 266, #31:20960–20964.

(List continued on next page.)

*Primary Examiner*—Lorraine Spector
*Assistant Examiner*—Eileen B. O'Hara
(74) *Attorney, Agent, or Firm*—Michael L. Dunn

(57) ABSTRACT

A specific, unique, natural biological factor that has the capacity to abate one or more of the toxic effects of TNF. This factor may have therapeutic potential in one or more of the diverse disease states in which TNF is known to have a causative role. The unique, approximately 27 kDa protein is designated TIP-$B_1$. TIP-$B_1$, when purified and added back to TNF sensitive cells, effectively ablates TNF-induced cell lysis and TNF-induced apoptosis; cytolytic effects are central to many TNF-mediated actions. The invention includes a protein designated TIP-$B_1$ purified to homogeneity. The protein has a molecular weight of about 27 kD. The protein is capable of inhibiting the action of TNF upon a cell, when said protein is introduced into extracellular medium surrounding the cell. The protein is free of sequences which interfere with normal cellular TNF binding sites and is free of sequences which directly bind to TNF. The invention further includes a method for using the protein for controlling TNF activity upon a cell.

4 Claims, 35 Drawing Sheets

OTHER PUBLICATIONS

Anthony W. Opipari, Jr. et al., "The A20 Zinc Finger Protein Protects Cells From Tumor Necrosis Factor Cytotoxicity," *The Journal of Biological Chemistry*, 1992. 267, #18:12424–12427.

Maria Jäättelä et al., "Major Heat Shock Protein hsp70 Protects Tumor Cells From Tumor Necrosis Factory Cytotoxicity," *The EMBO Journal*, 1992, 11, #10:3507–3512.

Patrick Mehlen et al., "Constitutive Expression of Human hsp27, Drosophila hsp27, or Human αB–Crystallin Confers Resistance to TNF– and Oxidative Stress–Induced Cytotoxicity in Stably Transfected Murine L929 Fibroblasts," *J. Immunol.*, 1995, 154:363–374.

Marja Jäättelä et al., "Heat Shock Proteins Protect Cells from Monocyte Cytotoxicity: Possible Mechanism of Self–Protection," *J. Exp. Med.*, 1993, 177:231–236.

Berish Y. Rubin et al., "Nonhematopoietic Cells Selected for Resistance to Tumor Necrosis Factor Produce Tumor Necrosis Factor," *J. Exp. Med.*, 1986, 164:1350–1355.

J.M. Boss et al., "Sensitivity to Tumour Necrosis Factor–Mediated Cytolysis is Unrelated to Manganous Superoxide Dismutase Messenger RNA Levels Among Transformed Mouse Fibroblasts," *Immunology*, 1991, 73:309–315.

Juan A. Melendez et al., "Reduced Expression of Manganese Superoxide Dismutase in Cells Resistant to Cytolysis by Tumor Necrosis Factor," *Free Radical Biology & Medicine*, 1992, 12:151–159.

Mitsuhiro Matsuda et al., "Protective Activity of Adult T Cell Leukemia–Derived Factor (ADF) Against Tumor Necrosis Factor–Dependent Cytotoxicity on U937 Cells," *The Journal of Immunology*, 1991, 147:3837–3841.

E.S. Berleth et al., "Purification and Characterization of Multiple Proteins from HEL Cells Which Inhibit TNFα–Induced Cytotoxicity," *Proc. AACR*, 36:467 (Abstract).

A.D. Henn et al., "TNF Inhibitory Protein–B1:A Novel Inhibitor of Tumor Necrosis Factor," *AACR*, 39:529 (Abstract) Mar. 1998.

* cited by examiner

*TIP-2 was a semipurified preparation with a known level of TNF inhibitory activity that was used as a positive control in the initial purification studies.

amino terminus:
    (A)-P-Y-T-V-V-Y-F-P-V-(R)-G-(R)-X-A-A-L-R
(SEQ. ID. #2)

Panel A: Control cells cultured for 24h, 11.25% subdiploid
Panel B: Cells cultured for 18h in medium and 6h in TNF + CHX, 28.78% subdiploid
Panel C: Cells cultured for 18h with TIP-B$_1$ and 6h with TNF+CHX, 13.05% subdiploid Mol. Wt. Std.
274 bp PCR product from BG((TNF) library
BG9(TNF) plasmid library
BG9(Control) plasmid library

```
GGCACGAGCACGGCGGCGGCGTCGTCTCCCGGCAGTGCAGCTGCCGCTACCGCC
 G  T  S  T  A  A  A  S  S  P  G  S  A  A  A  A  T  A
 |       M1       |           |       M2       |
GCCCTCTGCCCGCCGGCCCGTCTGTCTACCCCAGCATGAGCGGCCTGCGCGTC
 A  L  C  P  P  A  R  L  S  T  P  S  M  S  G  L  R  V

TACAGCACGTCGGTCACCGGCTCCCGCGAAATCAAGTCCCAGCAGAGCGAGGTG
 Y  S  T  S  V  T  G  S  R  E  I  K  S  Q  Q  S  E  V

ACCCGAATCCTGGATGGGAAGCGCATCCAATACCAGCTAGTGGACATCTCCCAG
 T  R  I  L  D  G  K //R  I  Q  Y  Q  L  V  D  I  S  Q
                    |   amidation    |
GACAACGCCCTGAGGGATGAGATGCGAGCCTTGGCAGGCAACCCCAAGGCCACC
 D  N  A  L  R  D  E  M  R  A  L  A  G  N  P  K //A  T
                                                 |   M3        |
CCACCCCAGATTGTCAACGGGGACCAGTACTGTGGGGACTATGAGCTCTTCGTG
 P  P  Q  I  V  N  G  D  Q  Y  C  G  D  Y  E  L  F  V
                                •••••••••••••••••••••••••••••••••••••
GAGGCTGTGGAACAAAACACGCTGCAGGAGTTCCTGAAGCTGGCT*TGA*GTCAAG
 E  A  V  E  Q  N  T  L  Q  E  F  L  K  L  A  (SEQ. ID. #7)
•••••••••••••••••••••••••••  |    CKII    |•••••••••••
CCTGTCCAGAGTTCCCCTGCTGGACTCCATCACCACACTCCCCCCAGCCTTCAC

CTGGCCATGAAGGACCTTTTGACCAACTCCCTGTCATTCCTAACCTAACCTTAG

AGTCCCTCCCCCAATGCAGGCCACTTCTCCTCCCTCCTCTCTAAATGTAGTCCC

CTCTCCTCCATCTAAAGGCAACATTCCTTACCCATTAGTCTCAGAAATTGTCTT

AAGCAACAGCCCCAAATGCTGGCTGCCCCCAGCCAAGCATTGGGGCCGCCATCC

TGCCTGGCACTGGCTGATGGGCACCTCTGTTGGTTCCATCAGCCAGAGCTCGCC

AAAGGCCCCGCAGTCCCTCTCCCAGGAGGACCCTAGAGGCAATTAAATGATGTC

CTGTTCCATTGAAAAAAAAAAAAAAAA (SEQ. ID. #6)
```

FIGURE 13

Preimmune

Untreated

Preimmune

50 U/ml TNF
18 hours

Antiserum 17

Untreated

Antiserum 17

50 U/ml TNF
18 hours

Pre-immune

Untreated

Antiserum
17

Untreated

Antiserum
17

50 U/ml TNF 18hrs

TUMOR NECROSIS FACTOR INHIBITORY PROTEIN TIP B$_1$ AND METHOD OF USING SAME

This invention was made with support by Federal Grant No. P01 CA 13038. The U.S. Government may have certain rights in this invention.

BACKGROUND OF THE INVENTION

This invention relates to the inhibition of the activity of tumor necrosis factor (TNF). TNF is known to have a causative role in many diseases such as chronic inflammation, certain types of arthritis, late stage wasting disease in cancer (cachexia), auto immune diseases such as lupus, and septic shock.

TNF is a cytokine which possesses multiple activities and affects almost every type of cell in the body. It was initially identified and named because of its ability to cause hemorragic necrosis of certain tumors in mice. It was subsequently recognized as the causative agent in the wasting condition in late stage cancer known as cachexia. A single gene codes for a membrane-bound 26 kD TNF protein; proteolytic cleavage produces circulating 17 kD TNF. Both are believed to be active. TNF is produced by most cells of the immune system, certain other cells and is constituitively produced in the thymus and by many leukemic cell lines.

TNF plays a critical role in the immune system and inflammation which may be ascribed to three different TNF functions. Evidence indicates that TNF is important in 1) facilitating leukocyte adhesion to and migration through endothelial cells by effects on remodeling of the extracellular matrix as well as on regulating cell adhesion molecules and integrins, 2) cell growth and differentiation and 3) programmed cell death (apoptosis) and cytotoxicity. The Immunopharmacology and Therapeutics section of the Department of Experimental Therapeutics (Grace Cancer Drug Center) has made a number of significant contributions toward clarifying the effects of TNF on host defense systems, and is currently using this information to develop effective anticancer therapies.

TNF's multiple activities may be explained in part by the existence of two receptors for TNF (molecular weights of 55 kD, TNFR1, and 75 kD, TNFR2). They are members of a TNFR superfamily which share considerable extracellular homology, indicating that they bind to similar ligands, but limited intracellular homology, suggesting that they may initiate different signal transduction/second messenger systems. Consistent with their assignment to this receptor superfamily, the TNFRs: 1) share extracellular homology and bind both TNF and lymphotoxin (TNFβ) with high affinity, and 2) have little intracellular homology, consistent with TNF's effects on a multitude of molecules involved with toxic/detoxification mechanisms and signal transduction. Recent evidence suggests that the cytoplasmic portions of the receptors bind different proteins, and that these proteins may also bind to other TNFR superfamily members.

The relative roles of TNFR1 and R2 signaling in TNF effects differ depending on the cells under investigation, and the effect examined. Both receptors are present on most cells, complicating the assignment of a specific effect to a specific TNFR type. Data indicate that TNFR1 stimulation, including receptor clustering, leads to cell lysis (both necrotic and apoptotic mechanisms have been reported); whether or not TNFR2 signaling contributes to this lysis is not always addressed. The "death domain", believed to signal lysis, at least in part through activation of the apoptotic pathway, is present in the cytoplasmic portion of both the TNFR1 and another TNFR superfamily member, Fas, whose binding also induces apoptosis. It is unclear if TNF and Fas induce apoptosis by the same mechanism. Several studies have linked activation of TNFR2, probably including clustering, to stimulation of proliferation, but TNFR2's role in TNF mediated lysis is less defined. It does appear that, under certain conditions, TNFR2 signaling and receptor clustering are responsible for a component of TNF mediated lysis.

A small number of transformed cell lines are sensitive to direct TNF cytotoxicity, but a greater number are TNF resistant. In the large majority of cases, TNF resistance of these cells does not appear to be correlated with a lack of TNF receptors or with defects in the internalization of the TNF-receptor complexes. In fact, many resistant cells are lysed by TNF when a protein synthesis inhibitor is present. This finding suggests that TNF induces/activates (at the mRNA level and/or the protein level) a protein or proteins which protect(s) the cell from TNF mediated lysis. TNF increases mRNAs for molecules related to cell adhesion, contact and substructure (ELAM-1/E-selectin, ICAM-1, VCAM-1, collagen, vimentin, collagenase, and stromelysin), certain cytokines and lymphokines (IL8 and MCAF/MCAP-1/murine JE), and several key transcription factors (p65 subunit of NF-kB, c-myc, c-jun, c-fos, and c-fra). A number of proteins/activities are known to be induced by TNF, although their respective mRNAs are not always found in TNF subtraction libraries. This suggests that TNF may also induce proteins at the translational/posttranslational level. TNF treatment of cells has been shown to result in increased secretion of a number of cytokines and immune factors (including IL6, IL8, IL1, CSF-1, GSCF and GMCSF) and receptors (MHC class I molecules, the p55 IL2 receptor and the EGF receptor).

Several proteins have been suggested, with varying numbers of supporting studies, as proteins which protect cells from TNF mediated lysis. However, their mechanisms of protection and their physiologic significance have yet to be elucidated. These proteins do not appear to protect the cells completely, and the investigators involved are in agreement that more than one protein is probably involved in protection of a given cell. These data are consistent with the hypothesis that multiple mechanisms contribute to TNF initiated lysis, and, therefore, the proteins which are protective to a cell correlate to the specific mechanism(s) by which that cell is lysed by TNF. Proteins which have been linked to protection from TNF induced lysis include: 1) manganese superoxide dismutase (MnSOD), an enzyme which converts toxic superoxide radicals to innocuous products, 2) plasminogen activator inhibitor 2 (PAI2), a cytosolic protein which is a member of the serpin family of protease inhibitors, 3) the ~80 kD protein encoded by the A20 clone of a TNF subtraction library, 4) heat shock protein (hsp) 70 and hsp 27, and 5) endogenous TNF. Most of the studies implicating these proteins in resistance to TNF cytotoxicity involve transfection and expression of the protein in cells which then show increased resistance, or surveys which show increased levels of these proteins in subclones with increased resistance. However, levels of activity or mRNA of these proteins do not always correlate with the degree of resistance.

U.S. Pat. No. 5,136,021, entitled "TNF-Inhibitory Protein and a Method of Production", discloses a TNF inhibitory protein named TIP. Subsequent to filing the patent, the amino-terminal amino acid sequence (10 amino acids) of TIP was determined to be V-V-X-A-V-X-L-X-A-H (SEQ. ID. #1). As this protein was in very low abundance and the purification procedure was extremely labor intensive and difficult, it was not possible to obtain sufficient material for internal amino acid sequencing. These sequences were necessary to facilitate the search for the TIP gene. An alternative simpler and more effective method to isolate a "TIP" was therefore needed.

BRIEF DESCRIPTION OF THE INVENTION

In accordance with the invention, a specific, unique, natural biological factor has been discovered that has the capacity to abate one or more of the toxic effects of TNF. This factor, therefore, may have therapeutic potential in one or more of the diverse disease states in which TNF is known to have a causative role. The unique, approximately 27 kDa protein is designated TIP-$B_1$. TIP-$B_1$, when purified and added back to TNF sensitive cells, effectively abates TNF-induced cell lysis and TNF-induced apoptosis; cytolytic effects are central to many TNF-mediated actions.

More particularly, the invention includes a protein designated TIP-$B_1$ purified to homogeneity. The protein has a molecular weight of about 27 kD. The protein is capable of inhibiting the action of TNF upon a cell, when said protein is introduced into extracellular medium surrounding the cell. The protein is free of sequences which interfere with normal cellular TNF binding sites and is free of sequences which directly bind to TNF.

The invention further includes a method for using the protein for controlling TNF activity upon a cell.

BRIEF DESCRIPTION OF THE DRAWINGS

FIG. 13 is a nucleotide sequence of Clone A (also called tip-SN) and its encoded amino acid sequence including the sequenced TIP-$B_1$ peptides A, B, C and consensus sequences for three myristylation sites (M1, M2 and M3), an amidation site, and a casein kinase II site (CKII).

DETAILED DESCRIPTION OF THE INVENTION $TIP-B_1$ as used herein means a protein having a molecular weight of about 27 kD which acts as an extracellular protein which inhibits the activity of TNF upon a cell, without binding to TNF or interfering with the binding of TNF to the target cell. $TIP-B_1$, as discussed in detail below, is obtained from lysed TNF treated cells by isoelectric focusing or an equivalent method.

In a particular example, in accordance with the invention, a simple four step protein purification method yielded a $TIP-B_1$ protein, having a molecular weight of about 27 kD, which has TNF inhibitory activity and is a unique protein. The amino-terminal amino acid sequence was determined to be A-P-Y-T-V-V-Y-F-P-V-R-G-R-X-A-A-L-R (SEQ. ID. #2) and, therefore, is different from the protein covered by U.S. Pat. No. 5,136,021.

Figure 1A:
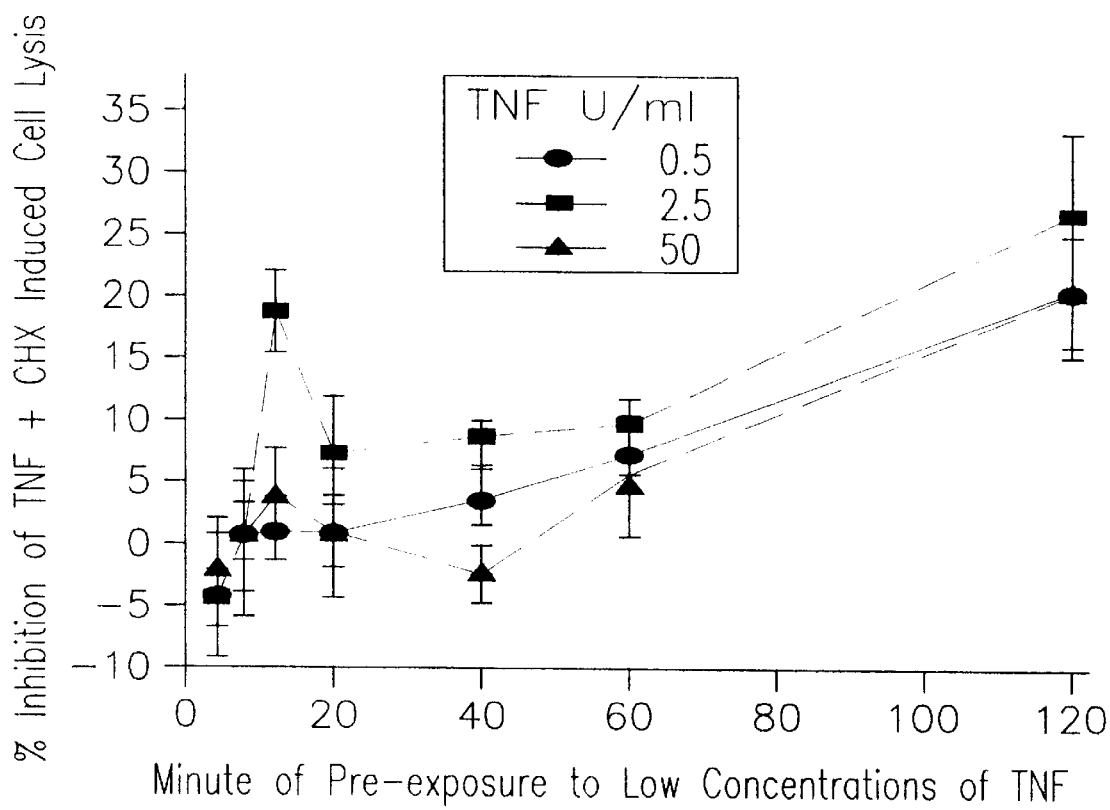
FIG. 1A is a graph showing kinetics of induction of protection from TNF+CHX lysis by pre-exposure to low concentrations of TNF.
Figure 1B:
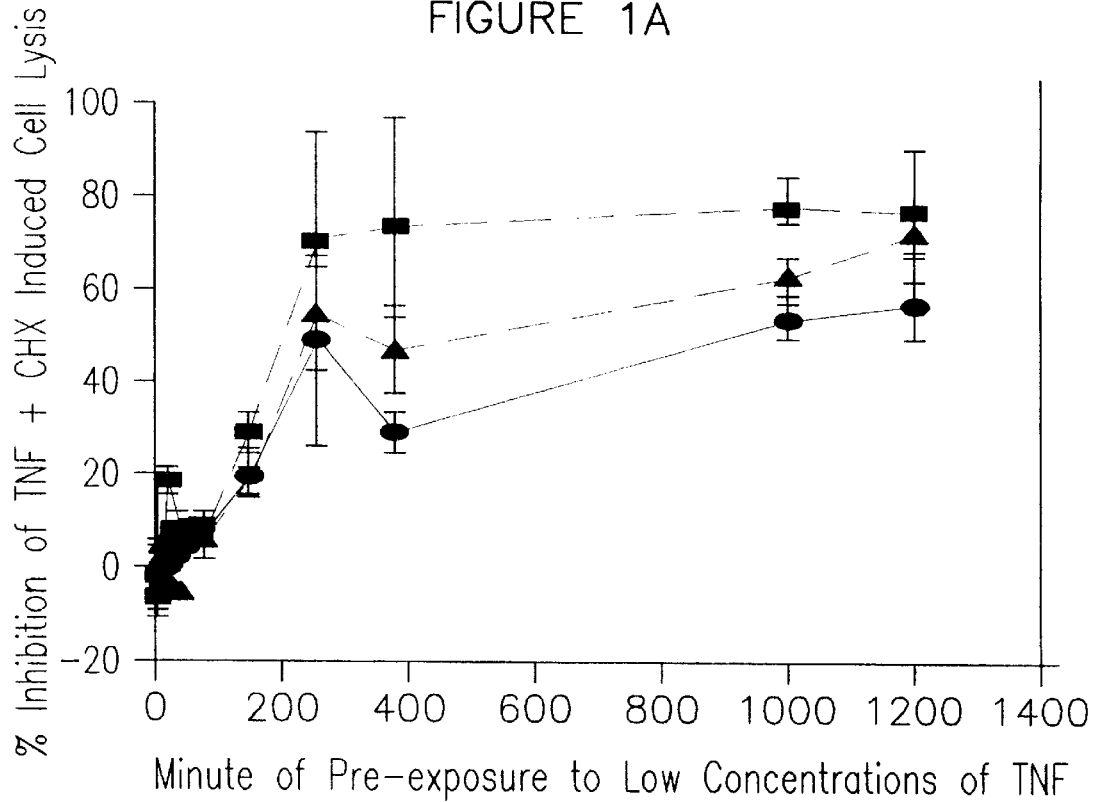
FIG. 1B is a graph showing kinetics of induction of protection from TNF+CHX lysis by pre-exposure to low concentrations of TNF.

Many cell lines which are lysed by appropriate concentrations of TNF alone or TNF plus macromolecular synthesis inhibitors such as cycloheximide (CHX) or actinomycin D are rendered refractory by pre-exposure to low concentrations of TNF. An example of such an effect is shown on FIGS. 1A and 1B. These data were obtained using the BG9 fibroblastoid cell line. Panel A shows the rapid onset (i.e. within 15 min. of exposure to 2.5 U/mL TNF) of a relatively modest level of protection and its equally rapid decay. Subsequently, a second inhibitory activity develops. It is detectable by 2 h, reaches a maximum by 4 h and is sustained for at least 20 h (FIGS. 1A and B). A similar TNF concentration dependence was noted for the induction of both the rapid onset and delayed protective activities; namely, the maximally effective concentration was ~2.5 U/mL and concentrations both lower (e.g. 0.5 U/mL) or higher (e.g. 50 U/mL) were less effective.

Experimental evidence was obtained indicating that: 1) this protective activity did not develop if a protein synthesis inhibitor was present during the period of pre-exposure to low concentrations of TNF, 2) cells pre-treated with the lysate from TNF-treated cells were protected from TNF-induced lysis, 3) the protective activity was present in the $10^5$ xg supernatant from sonicated TNF-treated cells.

Figure 2A:
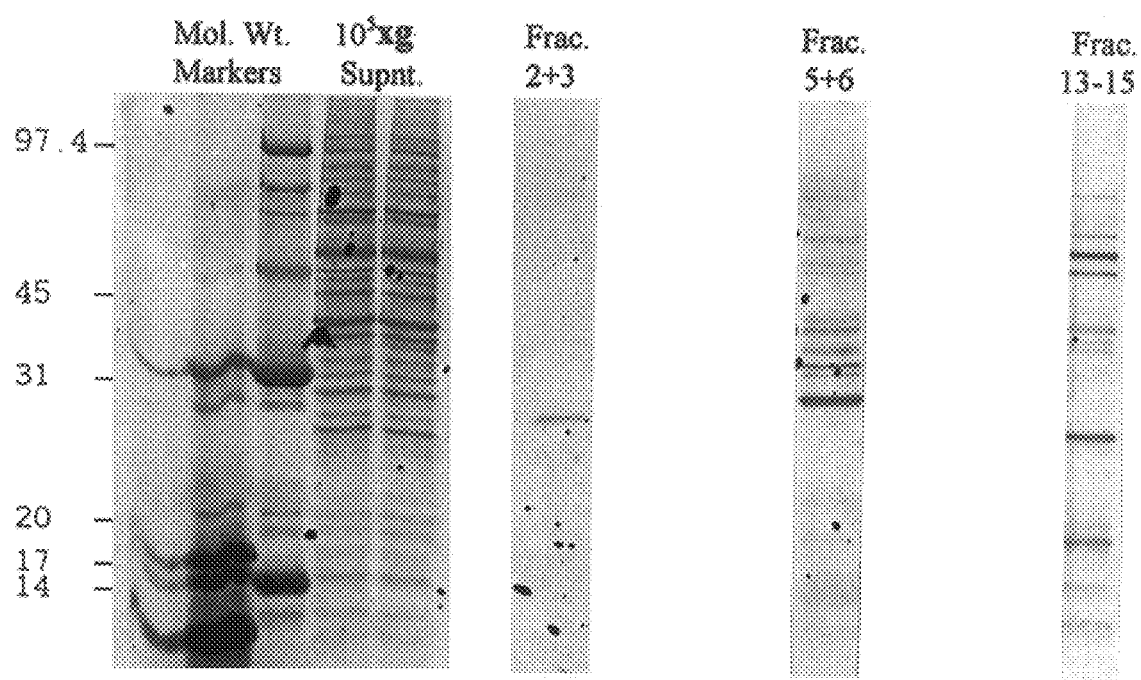
FIG. 2A is a gel showing isolation of three fractions with tip-like activity by isoelectric focusing on a Rotofor® apparatus.
Figure 2B:
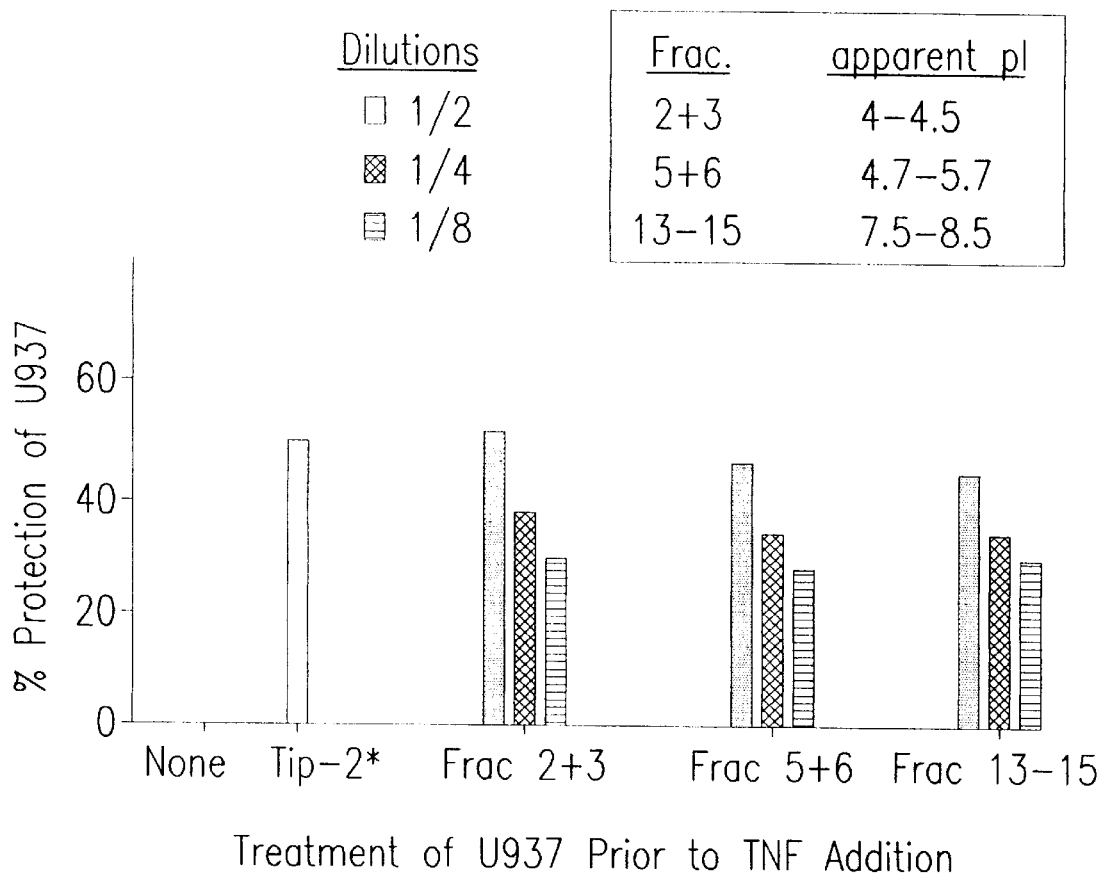
FIG. 2B is a graph showing percent protection of a cell line by exposure to the protein fractions isolated in FIG. 2A.

To obtain a specific $TIP-B_1$ protein, proteins in the $10^5$ xg supernatant from TNF-treated cells were subjected to isoelectric focusing using a BioRad Rotofor® isoelectric focusing apparatus and ampholytes covering the pH range of 3 to 10. The twenty fractions from the Rotofor® were analyzed for pH, protein content and protective activity. There were three peaks of activity. The fractions encompassing each of the three peaks were pooled and analyzed for activity and for molecular size by SDS-PAGE (FIGS. 2A and 2B). All three pooled fractions had similar levels of protective activity. The pool of Fractions 2 plus 3 (pI 4 to 4.5) appeared to have only one predominant protein on SDS-PAGE; whereas, the other two pools had a number of prominent proteins. Based on these observations, it was decided to concentrate initially on the protein in the pool containing fractions 2+3.

Figure 3A:
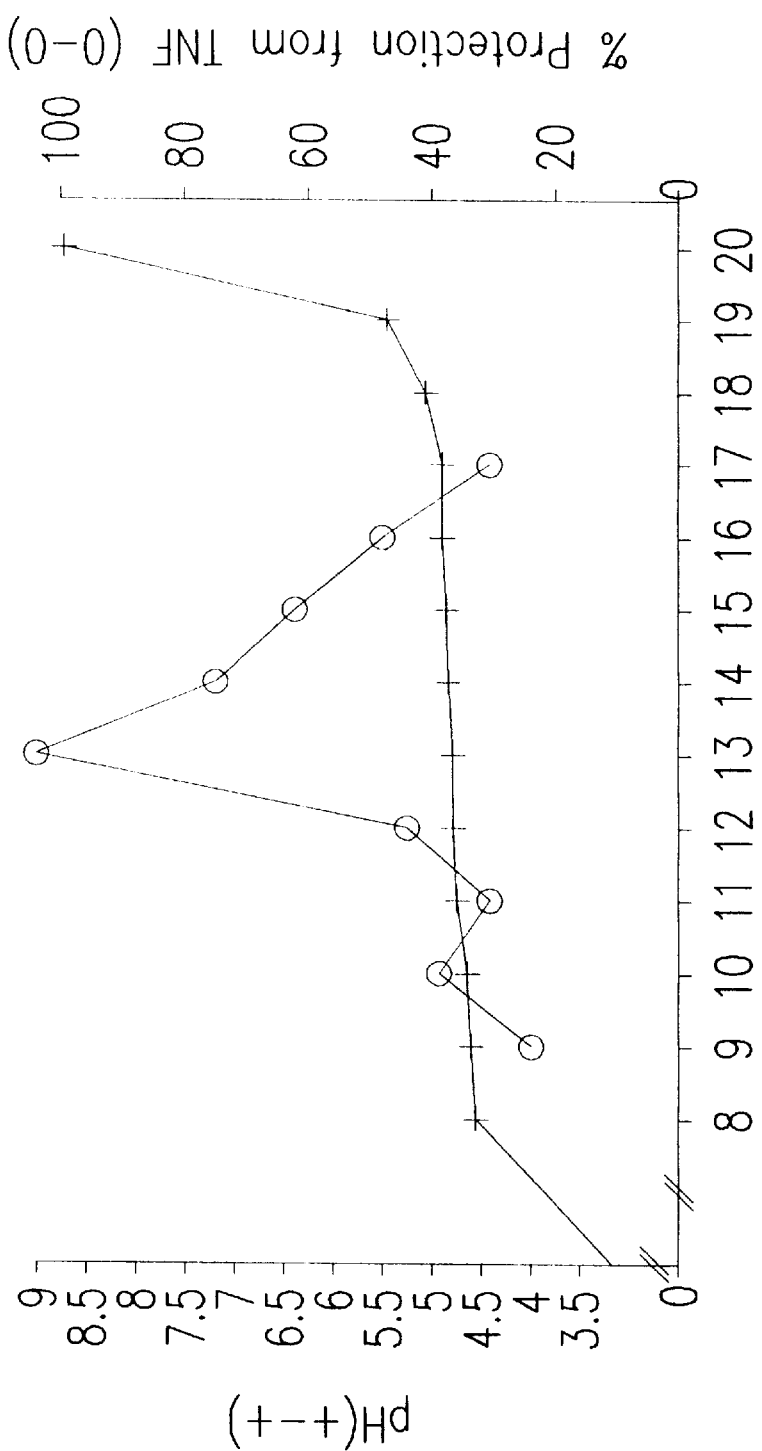
FIG. 3A is a graph showing protection by the proteins in Fraction 2+3 further resolved by Rotofor® refocusing—protective activity (protein fractions 9–17) and pH of resolved fractions 8–20.
Figure 3B:
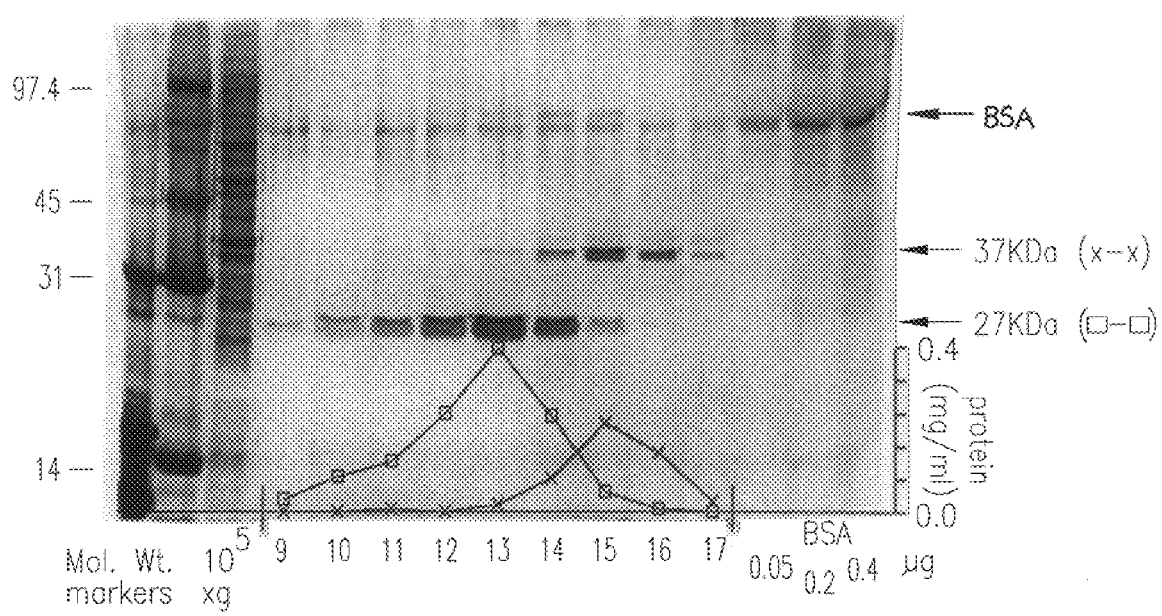
FIG. 3B is a gel and graph showing the distribution of the resolved 27 kDa and 37 kDa proteins in fractions 9–17.

The protein(s) in the 2+3 fractions combined from 5 separate Rotofor® runs were resolved into 20 fractions by a second Rotofor® separation. The ampholytes in the second separation were only those present in the 2+3 fractions from the initial 5 separations. The pH gradient formed in the second Rotofor® separation, therefore, was very shallow (FIG. 3A,+---+). All 20 fractions were analyzed for protein content and only those with detectable protein were analyzed further (fractions 8 and below and 18 and above did not have detectable protein). The protective activity profile for these 9 fractions (i.e. fractions 9–17) is shown in FIG. 3A and the SDS-PAGE analysis is shown in FIG. 3B. It can be seen that, when an equal volume of each fraction was tested, all fractions containing detectable protein had activity and the activity peaked in Fraction 13 at 100% protection. There were two proteins visible, a predominent ~27 kDa one (fractions 9–16) and a 37 kDa one of lower abundance (fractions 13–17). The amounts of the two proteins were estimated by densitometric analysis relative to the known amounts of BSA run on the same gel and are shown by the lines superimposed on the gel (FIG. 3B). The densitometric analysis indicated that the ~27 kDa protein peaked in Fraction 13, the same fraction in which the activity peaked (FIG. 3A). From the information available, it is possible that there is protective activity associated with both proteins; however, based on the coincidence of the peak of activity and the peak of abundance of the ~27 kDa protein and the lack of detectable 37 kDa protein in fractions 9–12, it was decided to investigate the ~27 kDa protein first.

Figure 4A:
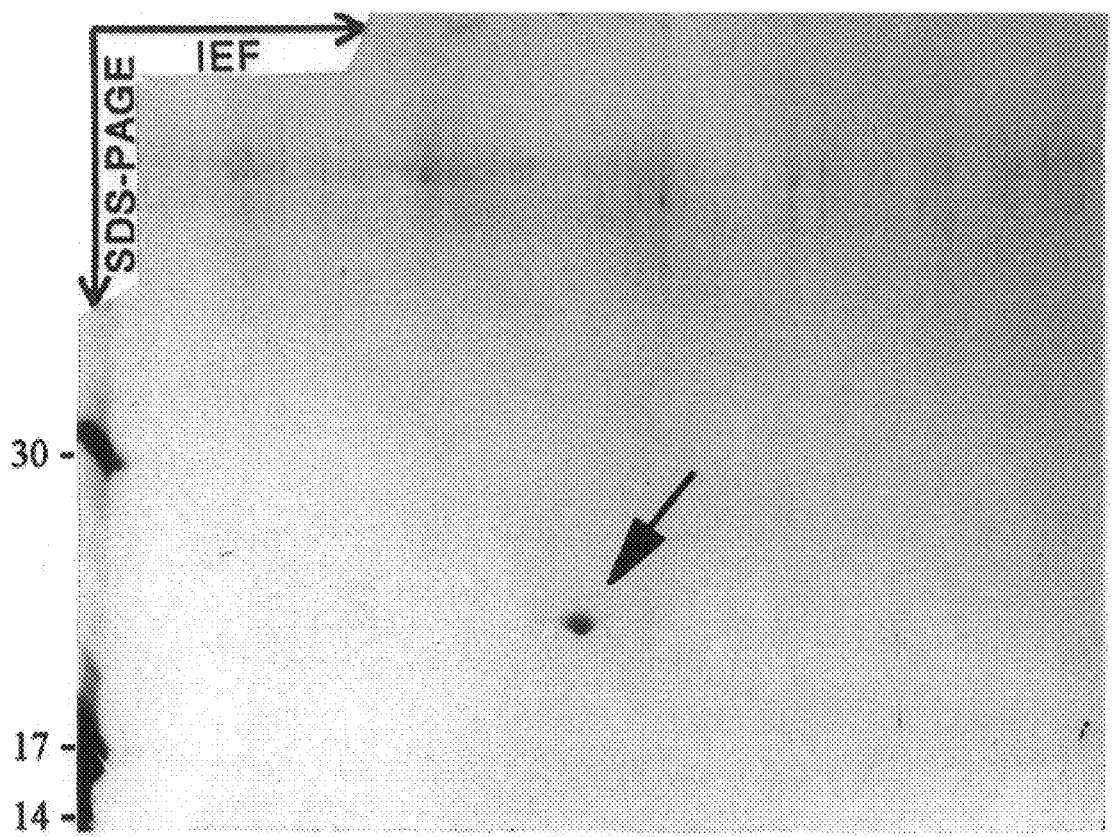
FIG. 4A shows a two dimensional gel analysis. Protein in pooled fractions 9–11 was resolved by isoelectric focusing (IEF, horizontal direction) followed by PAGE (vertical direction) and then silver stained. Molecular weight standards are visible on the left, the faint smear across the top is a staining artifact. The amino acids obtained from amino-terminal sequencing of pooled fractions 9–11 are shown.
Figure 4B:
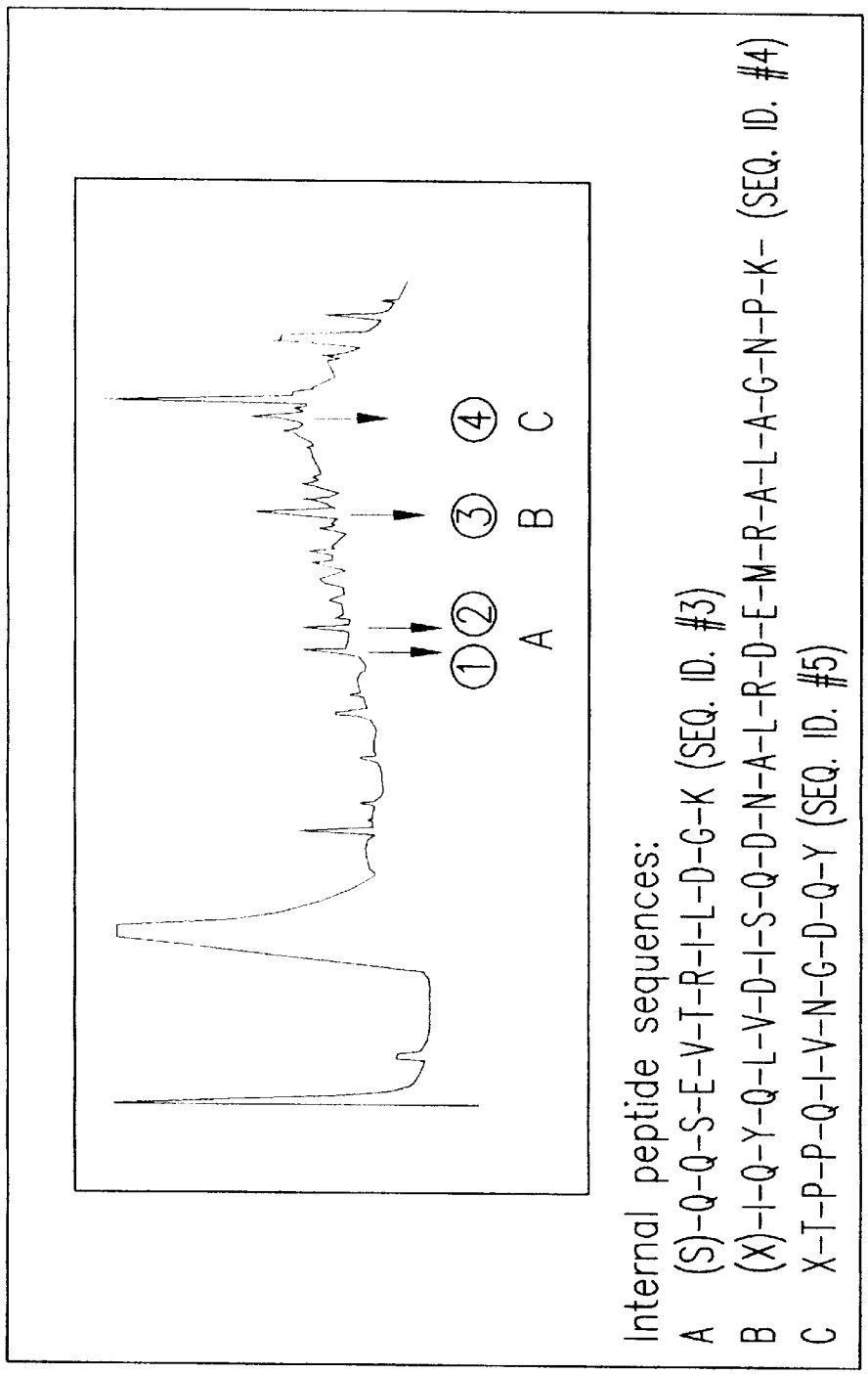
FIG. 4B shows the peptides selected for sequencing following HPLC separation of the products produced by the endoproteolytic cleavage of the ~27 kDa protein in pooled fractions 9–11 (FIG. 3). The amino acid sequences of peptides A, B and C are shown.

Fractions 9–11 were pooled. An aliquot was evaluated by two-dimensional gel electrophoresis and the material migrated as a single spot (FIG. 4A). A second aliquot was subjected to partial proteolysis with the endoproteinase LysC and the resulting peptides were separated by HPLC. Eight well-resolved peaks were collected. Four were selected for amino acid sequencing and were designated A–D (FIG. 4B). Sequence information was obtained on the three peptides designated A, B and C; the fourth apparently was amino-terminally blocked. The sequences obtained for the three peptides revealed 13, 27 (one, X, unidentified) and 12 (one, X, unidentified) amino acids, respectively. Namely: S-Q-Q-S-E-V-T-R-I-L-D-G-K (SEQ. ID. #3), X-I-Q-Y-Q-L-V-D-I-S-Q-D-N-A-L-R-D-E-M-R-A-L-A-G-N-P-K (SEQ. ID. #4), X-T-P-P-Q-I-V-N-G-D-Q-Y (SEQ. ID. #5). None of the sequences overlapped and the three internal sequences (a total of 52 amino acids, 2 not identified) had no significant homology with any sequences in either Swiss-Prot or PIR-Protein banks.

A comparison of the mass of the three peptides obtained by mass spectrometry with that derived from the determined amino acid sequence (determined either by amino acid sequencing, peptides A and B, or from the nucleotide sequence of Clone A, peptide C for which only a partial amino acid sequence was obtained) is shown in Table 1. The close agreement between the values determined in two different ways provides evidence that Clone A encodes a portion of TIP-B$_1$. Clone A is also designated as tip-SN and the protein product it encodes, i.e. the recombinant partial TIP-B$_1$, is referred to as r-TIP-B$_{1P}$.

TABLE 1

Comparison of the Mass of HPLC Purified Internal Peptides A, B and C Obtained by Mass Spectrometry with that Derived Based on Amino Acid Sequence (Determined or Nucleotide Translated).

| Peptide | # of sequenced amino acids | observed mass | predicted mass based on amino acid sequence | predicted mass based on translation of clone tip-SN |
|---|---|---|---|---|
| A | 13 | 1461.2 g | 1461.54 | 1461.5 |
| B | 26 | 3115.0 g | 3116.5 | 3116.5 |
| C | 11 | 3761.0 g | 1307.5 | 3788.57 |

A third aliquot of the pooled fractions (9–11) was analyzed to determine the protein's amino-terminal sequence and an 18 amino acid long sequence was obtained. The amino-terminal sequence, A-P-Y-T-V-V-Y-F-P-V-R-G-R-X-A-A-L-R (SEQ. ID. #2), was confirmed by independently sequencing the material in the pool of fractions 2+3 from a different batch of TNF-induced cells. The amino-terminal sequence corresponds to the first 18 amino-terminal residues of human fatty-acyl-ethyl-ester synthase III (FAEES III), a 26 kDa (pl 4.9) protein which catalyzes the addition of ethanol to fatty acids, and has been postulated to be an important enzyme in the detoxification of xenobiotics. FAEES III shares 98% homology with the placental acidic glutathione transferase (GST). FAEES III can also catalyze glutathione transfer. An aliquot of pooled fractions 9–11 did not have GST activity when assessed using 2,4 dinitrochlorobenzene, a standard substrate. Thus, despite amino-terminal (18 amino acids) homology to two known enzymes, the protein does not have comparable catalytic activity and three non-overlapping, internal peptide sequences (52 amino acids) had no homology with known proteins. It was concluded, therefore, that this was a unique, previously uncharacterized protein and it was named TNF inhibitory protein B$_1$ (TIP-B$_1$).

As shown in Table 2, cells pretreated in the standard assay with either Fraction 9–11 or Fraction 13 were protected from TNF-induced lysis in a concentration dependent manner (note that, at a 1:8 dilution, Fraction 13 was able to protect 100% of the cells). In contrast, TIP-B$_1$ added together with TNF did not protect the cells, regardless of whether or not the TIP-B$_1$ and TNF had been incubated together for 10 h prior to addition to the cells. Thus, TIP-B$_1$ does not simply neutralize TNF and for cells to be protected from TNF-induced lysis they must be pretreated with TIP-B$_1$. TIP-B$_1$ was demonstrated to be effective in protecting a number of different cell lines, e.g. MLD, U937 and BG9, from TNF-induced lysis.

TABLE 2

The Effect of Preincubation of TIP-B$_1$ and TNF on TNF plus CHX Mediated Lysis of MLD Cells in Comparison to TIP-B$_1$ Induced Protection in the Standard Assay.

| | % Protection[a] | |
|---|---|---|
| Test Agent | STD Assay | TIP-B$_1$ + TNF (±10 h@37°) |
| Frac 9–11 (1:8) | 22 | 0 |
| Frac 9–11 (1:16) | 9 | 0 |
| Frac 13 (1:8) | 115 | 5 (NS)[b] |
| Frac 13 (1:16) | 60 | 7 (NS)[b] |

TABLE 2-continued

The Effect of Preincubation of TIP-B$_1$ and TNF on TNF plus CHX Mediated Lysis of MLD Cells in Comparison to TIP-B$_1$ Induced Protection in the Standard Assay.

| | % Protection[a] | |
|---|---|---|
| Test Agent | STD Assay | TIP-B$_1$ + TNF (±10 h@37°) |

For the "STD assay", TIP-B$_1$ fractions (see FIG. 3) or medium were added to MLD cells. 10 hours later medium, TNF, and CHX were added. 18 hours later the cells were stained with crystal violet. Final concentrations were 500 U/ml TNF and 100 μg/ml CHX.
For the other two assays, TIP-B$_1$ was either preincubated with TNF for 10 hours at 37° C., and then both were added together with CHX or all three were added together (cells were preincubated with medium alone). Lysis was determined 18 hours later. The results obtained were identical and only one set is shown. All appropriate controls were run in parallel. "N" = 14 for medium alone, 9 for TNF + CHX alone, and 5 for all other groups.
[a]% protection was determined using the Absorbance$^{570}$ (Abs) readings from a plate reader as follows: 100 [(Abs. TIP-B$_1$ + TNF + CHX - Abs. TNF + CHX)/(Abs. medium alone - Abs. TNF + CHX)]
[b]Based upon the fact that the S.D.s for the mean (n = 5) values for these two observations were quite large, it is considered that they are not different from background.

Figure 5:
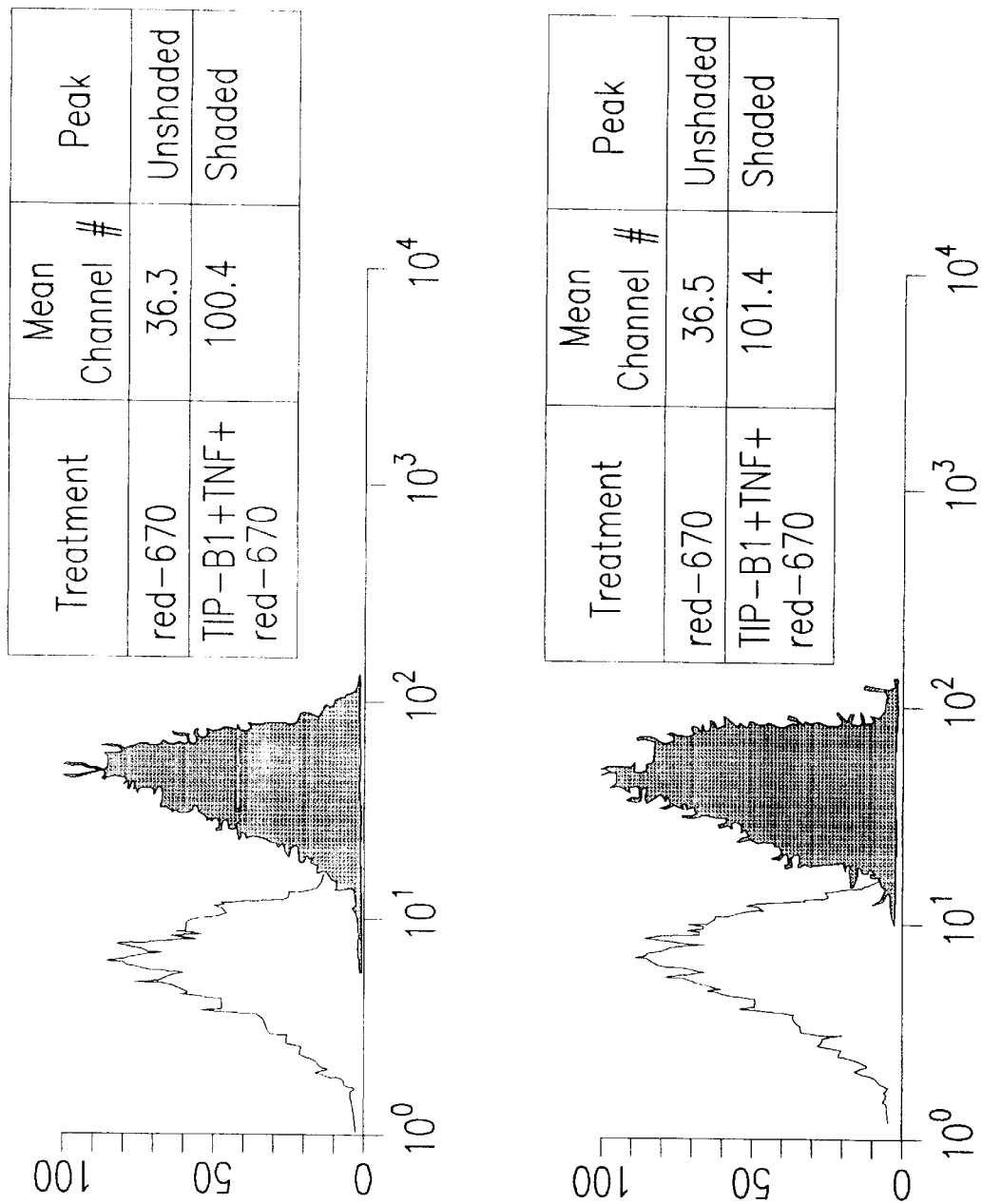
FIG. 5 demonstrates that preincubation of U937 cells with TIP-$B_1$ does not change TNF binding capacity. $5 \times 10^5$ U937 cells were incubated without any addition (top panel) or with TIP-$B_1$ (bottom panel) for 6 hours. The cells were incubated with medium or biotinylated TNF, washed, incubated with Streptavidin-red-670, fixed, and analyzed on a flow cytometer. Unlabeled TNF was capable of competing with biotinylated TNF for binding in a concentration dependent manner (data not shown). U937 $^{51}Cr$ release assays run in parallel showed TIP-$B_1$ inhibited TNF mediated lysis in a concentration dependent manner; for the conditions shown, inhibition was 20%.

TIP-B$_1$ does not alter the binding of biotinylated TNF to the cells (FIG. 5). Flow cytometric analysis indicated that the pretreatment of the cells with TIP-B$_1$ did not alter their ability to bind TNF. Aliquots of the same TIP-B$_1$ treated cells were protected from lysis and unlabelled TNF was able to compete with biotin-labelled TNF for binding in a concentration dependent manner (data not shown).

Figure 6:
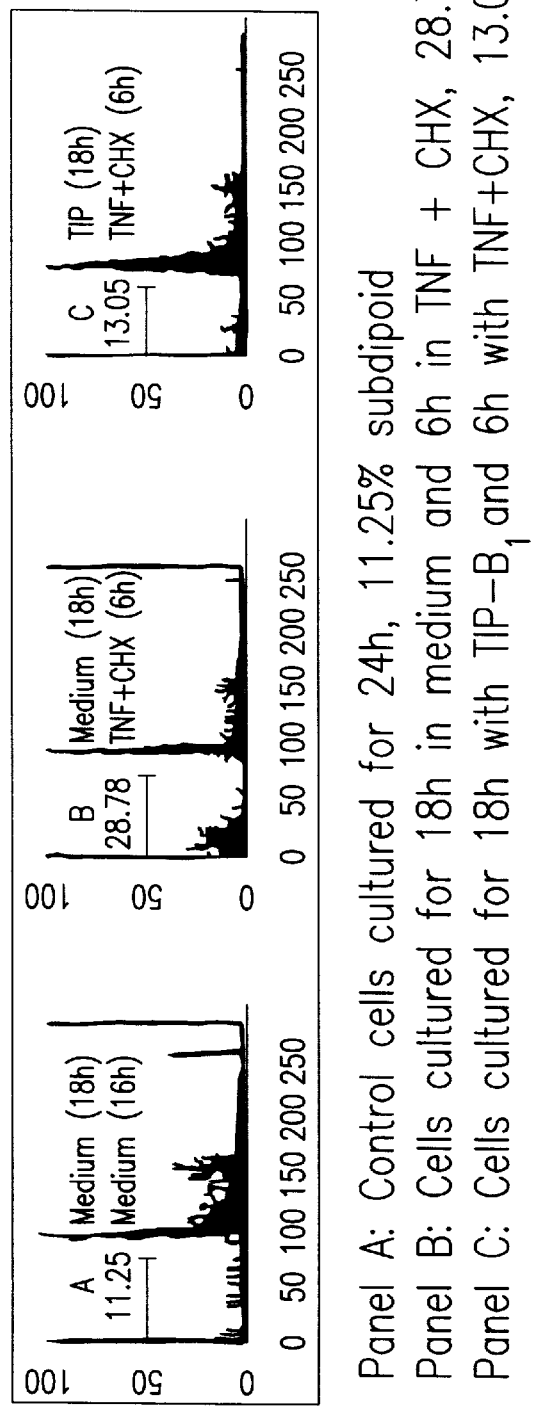
FIG. 6 is a series of graphs showing that TIP-$B_1$ protects U937 cells from TNF-induced apoptosis assessed based on percentages of total (10,000) events found in the subdiploid propidium iodide labeled DNA peak.
Panel A: control cells cultured for 24 h in medium, 11.25% subdiploid.
Panel B: cells cultured for 18 h in medium and 6 h in TNF+CHX, 28.78% subdiploid.
Panel C: cells cultured for 18 h with TIP-$B_1$ and 6 h with TNF+CHX, 13.05% subdiploid.
Figure 7:
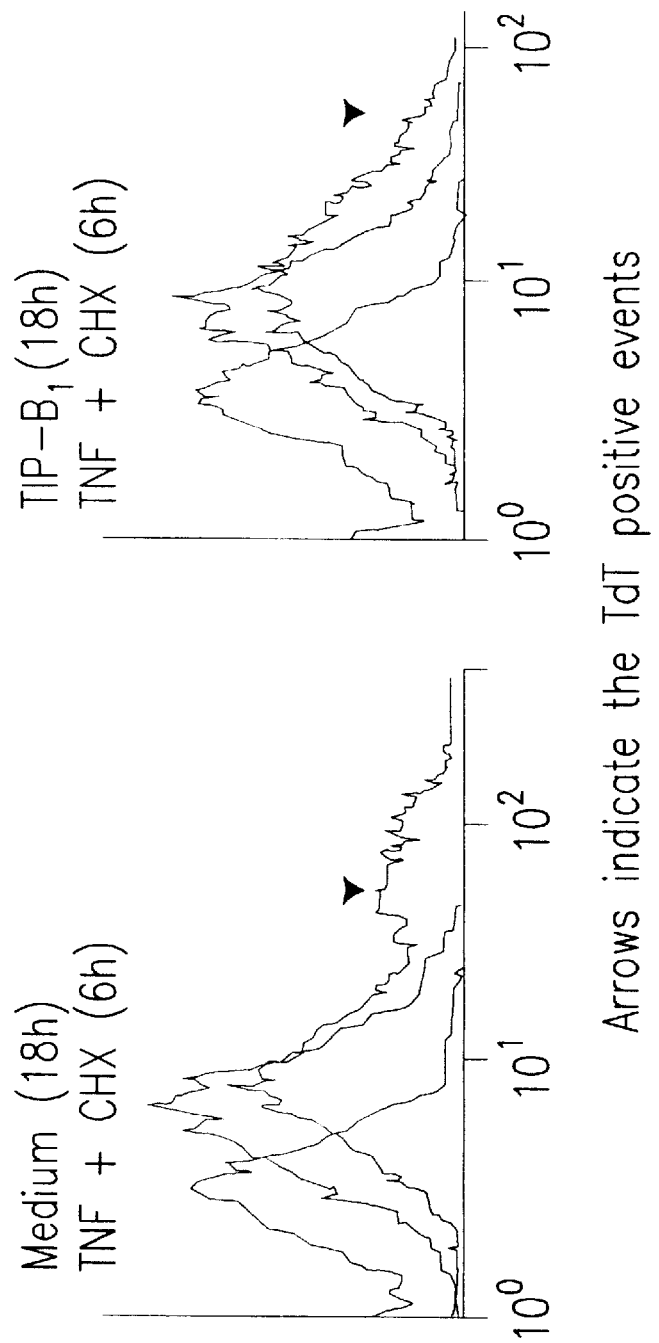
FIG. 7 is a series of graphs showing that TIP-$B_1$ protects U937 cells against TNF mediated lysis. Arrows indicate the TdT positive events (also, see Table 3).

TIP-B$_1$ was effective in protecting against apoptosis. This was shown by assessing apoptosis by the appearance of a subdiploid peak in propidium iodide labeled DNA studies, FIG. 6 (A–C), and in terminal deoxy transferase reactivity studies, FIG. 7. In the latter study, the effect of TIP-B$_1$ on apoptosis was compared to its effect on $^{51}$Cr release, a measure of membrane disruption, and protection from both was seen (Table 3).

TABLE 3

TIP-B1 protects U937 cells against TNF mediated lysis (including apoptosis). Lysis was determined similarly to that described for the "STD assay" in Table 2, except the U937 cell targets were prelabeled with $^{51}$Cr, and protection was determined by the radioactivity released into the supernatant. Apoptosis was measured by flow cytometric analysis of the specific fluorescein label incorporated following fixation in formaldehyde and incubation with TdT enzyme and fluorescein labeled-dUMP.

| | LYSIS % Specific $^{51}$Cr Release (% Protection) | | APOPTOSIS Specific TdT$^+$ Events (% Protection) |
|---|---|---|---|
| ASSAY | 6 hr | 10 hr | 6 hr |
| TNF | 16 | 24 | 1000 |
| TIP-B$_1$(1:8) + TNF | ND[a] | 12 (50) | 0 (100) |
| TIP-B$_1$(1:16) + TNF | ND | 13 (46) | 600 (40) |
| TNF + CHX | 40 | 53 | 2700 |
| TIP-B$_1$(1:8) + TNF + CHX | 16 (60) | ND | 1300 (52) |
| TIP-B$_1$(1:16) + TNF + CHX | 18 (55) | ND | 1800 (33) |

[a]ND not determined

Double stranded phagemid (ZAP®) cDNA libraries were constructed using mRNA from TNF-treated BG9 cells and untreated BG9 (control) cells following an assymetric PCR-based subtraction protocol. Briefly, single strand phagemid recombinants were produced from the two libraries. The control library was amplified (by PCR) in the presence of biotinylated UTP, and the biotinylated PCR-amplified single stranded DNA inserts were hybridized to the single strand phagemid recombinants from TNF-treated cells. The recombinants that did not hybridize were removed and split into two aliquots; one aliquot was used to transform an appropriate strain of E.coli to produce the first cDNA subtraction library, the other aliquot was rehybridized to another batch of biotinylated PCR-amplified product derived from the control library and the recombinants that did not hybridize were separated and used to transform E.coli to produce the second cDNA subtraction library.

Figure 8A:
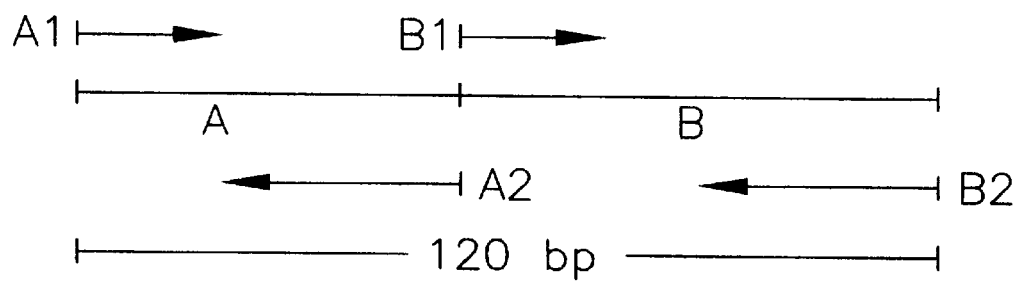
FIG. 8A is a map of primers used to generate a TIP-$B_1$ specific PCR product from a cDNA library from TNF-treated BG-9 cells. The location of degenerate oligonucleotide primers, based on the amino acid sequence of TIP-$B_1$ internal peptides A and B, that were used to generate a 120 bp PCR product encoding these peptides are shown.
Figure 8B:
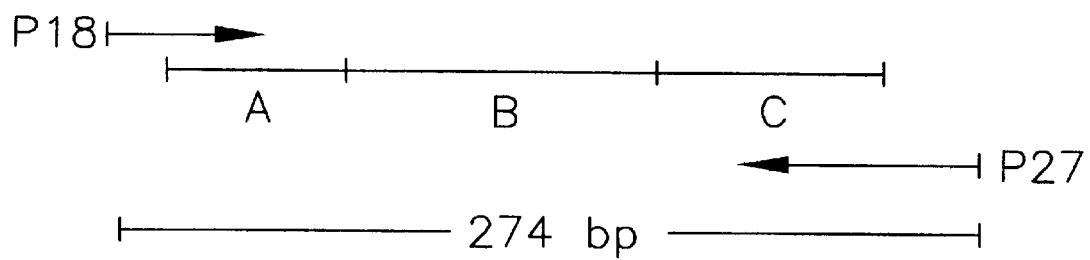
FIG. 8B is a map of primers used to generate a TIP-$B_1$ specific PCR product from a cDNA library from TNF-treated BG-9 cells. P18 and P27 TIP-$B_1$ specific oligonucleotide primers were used to generate a 274 bp PCR product from TNF-treated BG-9 cell cDNA.
Figure 9A:
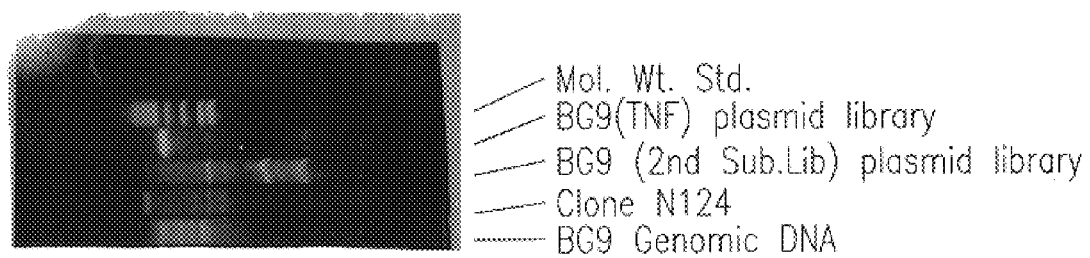
FIG. 9A is an agarose gel electrophoresis of the 274 bp PCR product derived from various DNA samples: TNF-treated BG9 cDNA library, BG9 second subtraction cDNA library and genomic DNA.

Using degenerate primers based on the amino acid sequence of peptides A and B, PCR analysis of the cDNA library from TNF-treated cells led to the generation of a 120 bp fragment (FIG. 8A). The formation of this fragment suggested that peptides A and B were oriented in tandem (head to tail) as shown in FIG. 8A. Subsequently, PCR amplification primers (Primers P18 and P27, FIG. 8B) were selected based on the partial sequence provided by an outside commercial laboratory. PCRs were conducted on the first subtraction library (containing 1000 cDNA clones), the second subtraction library (containing 30 cDNA clones), a cDNA library from TNF-treated cells (containing approx. 10$^6$ independent clones) and BG9 genomic DNA. A 274 bp fragment was generated from the first subtraction library (a faint band, not shown), the cDNA library from TNF-treated cells (a strong band) and BG9 genomic DNA, but not from the second subtraction library (FIG. 9A). This 274 bp fragment was subcloned and then sequenced. The sequence revealed that it contained the coding region for the 52 amino acids of the three TIP-B$_1$ internal peptides (A, B and C) in tandem (FIG. 8B). The two amino acids not identified by amino acid analysis (page 14) were now deduced based on the nucleotide sequence to be arginine and alanine.

Figure 9B:
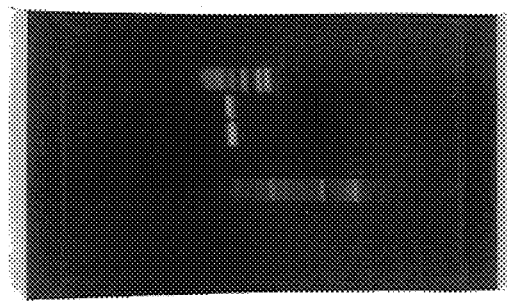
FIG. 9B is an agarose gel electrophoresis of the 274 bp PCR product derived from various DNA samples showing the comparison between the product derived from TNF-treated and control BG9 cells, along with the purified 274 bp fragment, obtained above, used as a reference standard.

To evaluate the potential for TNF induction of the corresponding message, and to estimate the abundance of this message in untreated cells and TNF-treated cells, the same primers as above (P18 and P27) were used, and PCR analyses of cDNA libraries from BG9 cells that were either not treated or treated with TNF for 16–18 hrs were carried out. The library from the TNF-treated BG9 cells, as expected, produced the 274 bp band, while the control library yielded a very faint band (FIG. 9B), suggesting that TNF induces TIP-B$_1$ message. To confirm this, a northern blot prepared with very limited amounts of mRNAs from TNF-treated and untreated cells was probed with the labeled 274 bp fragment. The results, normalized to G3PDH message, revealed ~1.6-fold induction. After having established, as detected by the 274 bp probe, the presence of more TIP-B$_1$ message in TNF-treated cells than in untreated cells, the cDNA library from the TNF-treated cells was screened in an effort to isolate the TIP-B$_1$ cDNA clone(s).

Figure 10:
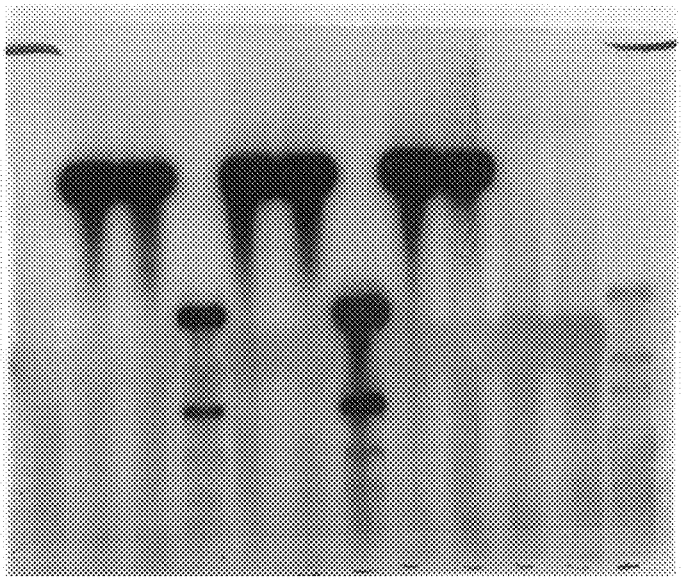
FIG. 10 is a Southern blot analysis of the eight putative TIP-$B_1$ cDNA clones probed with the 274 bp insert encoding the three internal TIP-$B_1$ peptides.
Figure 11:
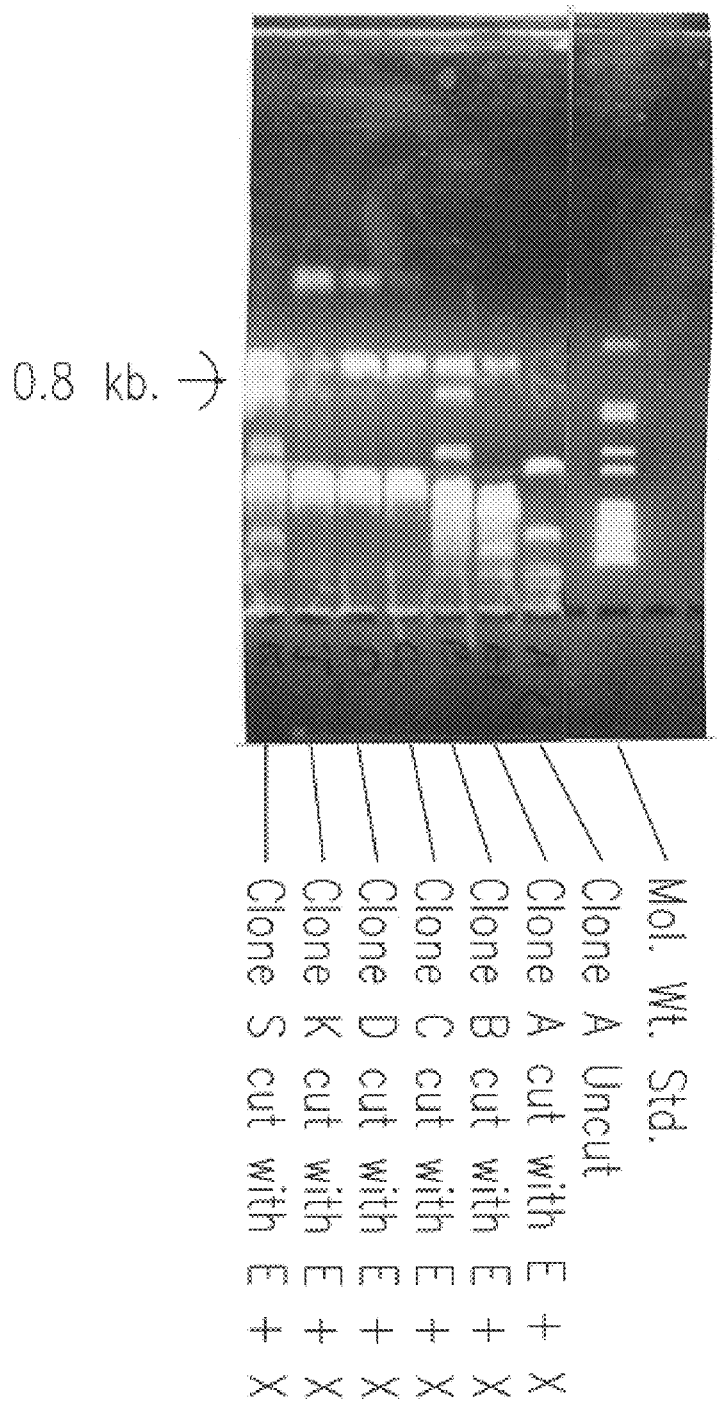
FIG. 11 is an agarose gel electrophoresis of the restriction enzyme digests of the plasmids derived from bacterial clones used in FIG. 10 revealing the 0.8 kb insert. These six clones have been given the letter designations A, B, C, D, K and S. In addition to the restriction fragments visible on the copy, faint additional bands were observed for C (0.3/0.4 kb) and D (0.9+0.3).
Figure 12:
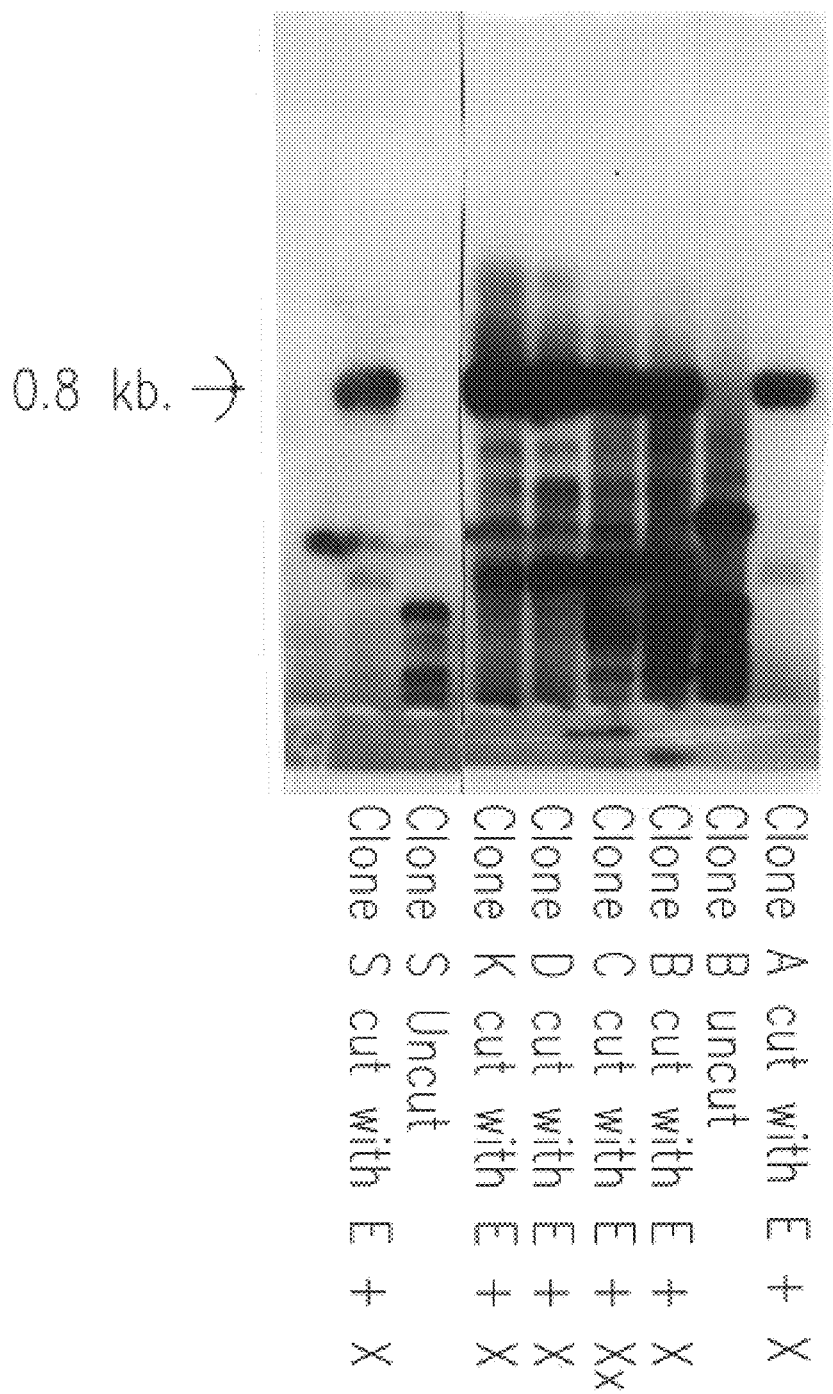
FIG. 12 is a Southern blot analysis of the six putative TIP-$B_1$ clones (A, B, C, D, K and S). The plasmids were restricted, separated on agarose gels, transferred to a membrane and then exposed to the $^{32}P$-274 bp probe.

The 274 bp insert was used to screen 150,000 plasmid-containing bacterial colonies derived from unidirectional phage recombinants that contained cDNA inserts corresponding to mRNAs from TNF-treated BG9 cells. On the third rescreening with increasing stringency, 8 colonies that hybridized with the 274 bp fragment were picked for stock cultures. Six colonies released an ~0.8 kb fragment upon digestion with EcoR1 (E) and Xho (X) (or E alone in some cases). These 0.8 kb fragments hybridized to the 274 bp fragment on Southern analysis (FIG. 10). These 6 colonies were designated as A, B, C, D, K and S and, on the basis of preliminary restriction enzyme analysis carried out on miniplasmid preparations, were characterized as follows: Clone A released a ~0.8 kb fragment; Clones B and S each released two fragments of ~0.8 kb and 0.9 kb; Clone C released a 0.8 kb fragment and a faint 0.3/0.4 kb fragment; Clones D and K released two fragments (0.8 kb and 0.9 kb) and a small (0.3/0.4 kb) faint fragment (FIG. 11). These results suggested that the cDNA inserts of these clones, most likely, were of the following sizes: A, ~0.8 kb; B and S, ~1.7 kb; D and K, ~2.0 kb; and C, ~1.1 kb. Southern blots of these inserts probed with the 274 bp fragment are shown in FIG. 12. As can be seen, the ~0.8 kb fragments from all these clones hybridized to the 274 bp fragment. The ~0.8 kb Clone A insert was sequenced (780 bp), and was found to contain the 274 bp sequence that encodes the 52 amino acids of TIP-B$_1$ internal peptides (FIG. 13). It was concluded, therefore, that Clone A is a partial message for TIP-B$_1$. Subsequent evaluation of Clones B, S, C, and D indicated that they were not TIP-B$_1$ message. FIG. 13 also shows the consensus sequences for three myristylation sites (M1, M2, and M3), an amidation site, and a casein kinase II site (CKII).

Figure 14A:
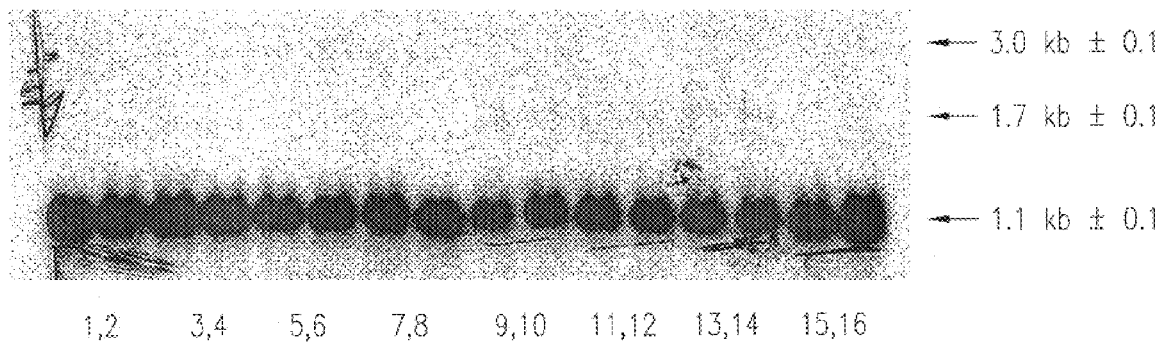
FIG. 14A is a Northern blot analysis of RNA isolated at different times from BG9 cells following treatment with TNF and probed with Clone A insert. RNA samples were resolved by formaldehyde agarose gel electrophoresis, transferred to a membrane which was probed with $^{32}P$-insert from Clone A. Lanes are: 1,2-2 h C; 3,4-2 h TNF; 5,6-6 h C; 7,8-6 h TNF; 9,10-12 h C; 11,12-12 h TNF; 13,14-24 h C; 15,16-24 h TNF. Film exposure time 12 hr.
Figure 14B:
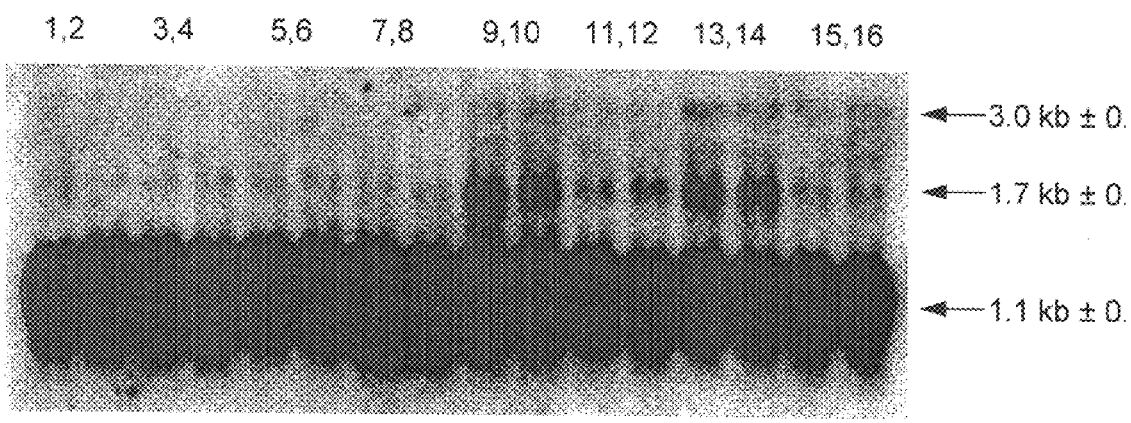
FIG. 14B is the Northern blot of FIG. 14A with a film exposure time of 36 hrs.

To determine the size of the complete TIP-B$_1$ message, the insert from Clone A (0.8 kb) was used to probe northern blots of RNAs from control and TNF-treated BG9 cells harvested at various times (up to 24 hrs) following treatment with TNF. It was found that the 0.8 kb insert from Clone A hybridized with three messages, 1.1, 1.7 and 3.0 kb (FIGS. 14A and 14B). It strongly hybridized with 1.1 kb (FIG. 14A), and weakly hybridized to 1.7 and 3.0 kb, as indicated by the longer exposure time required for their visualization (FIG. 14B). These results suggest that the Clone A insert recognizes three messages, and that possibly the 1.1 message is much more abundant than the 1.7 and 3.0 kb messages or that the insert shares more homology with the 1.1 message than with the other two. As had been suggested earlier with the 274 bp as probe, careful analysis, relative to G3PDH message, indicated that the 1.1 kb message was induced 1.7 fold by TNF after 20–24 h treatment of BG9 cells (Table 4).

TABLE 4

Induction of TIP-B$_1$-Specific Message Following Treatment of BG9 Cells with TNF[a]

| TIME | BG9 (Arbitary Units[b]) | | | TNF-Treated BG9 (Arbitary Units[b]) | | | TNF Induction |
|---|---|---|---|---|---|---|---|
| | A Insert | G3PDH | Ratio (X) | A Insert | G3PDH | Ratio (Y) | Y/X |
| 12 hr. | 1807 | 4636 | 0.389 | 2216 | 4970 | 0.446 | 1.15 |
| 24 hr. | 1941 | 6078 | 0.319 | 3252 | 5873 | 0.554 | 1.73 |

[a]BG9 cells were treated with TNF (1000 U/ml medium) for the indicated times. Total RNA was isolated from the cells and used in northern blot analysis. Briefly, the RNA was resolved by formaldehyde gel electrophoresis, transferred to Genescreen plus membranes and probed with $^{32}$P-labeled Clone A insert. The membranes were stripped and reprobed with $^{32}$P-labeled G3PDH probe and the autoradiograms were scanned using a laser densitometric scanner.
[b]Integrated volume points obtained from laser densitometric scan.

Figure 17:
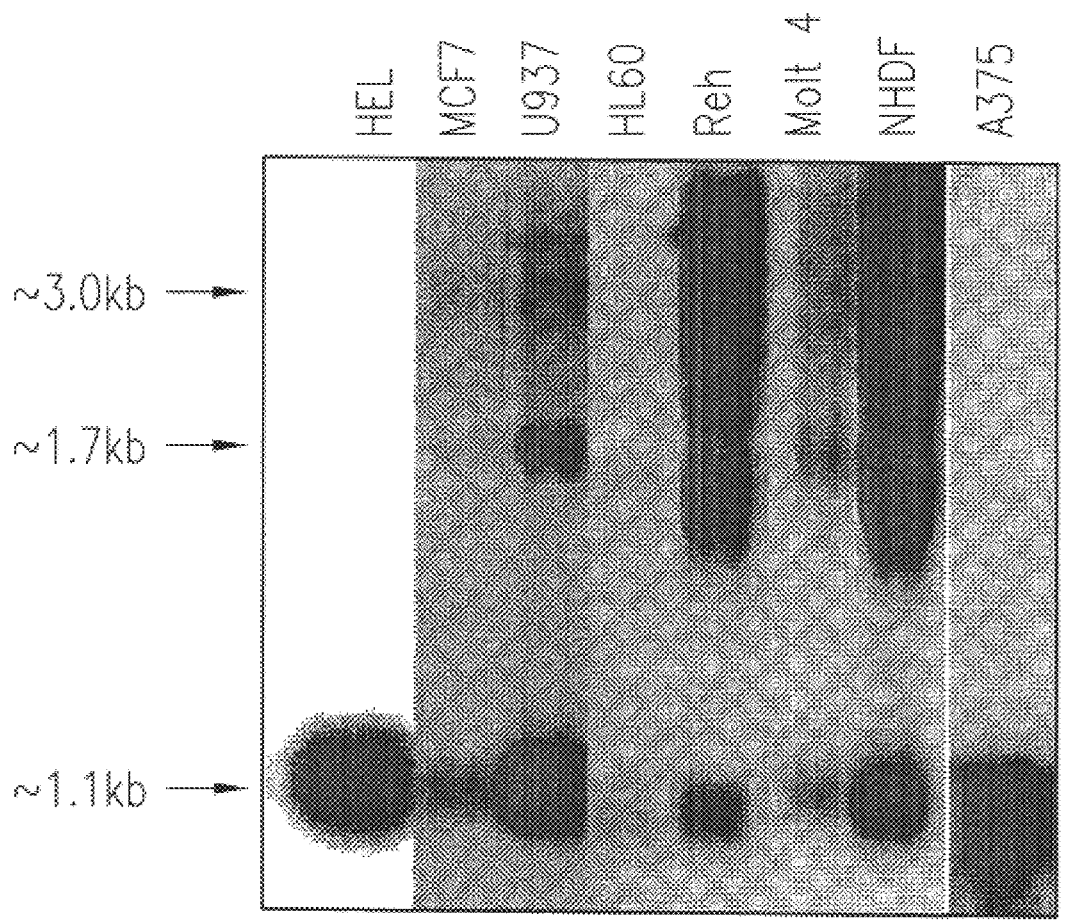
FIG. 17 is a Northern blot hyridization of Clone A with RNA from various cell types.

Using the Clone A insert as a probe, northern blots of mRNA from a number of cell types including those shown in FIG. 17 below, were examined. Such examined cell lines include: human embryonic lung fibroblasts HEL, mammary adenocarcinoma MCF7, histocytic lymphoma U937, promyelocytic leukemia HL-60, acute lymphoblastic leukemia REH, lymphoblastic T cell leukemia Molt 4, normal human diploid fibroblasts NHDF, and malignant melanoma A375. As was shown in FIG. 14, three size messages were seen. Twenty cell types in total have been examined to date, including 2 from mice, 2 from rats and 16 from humans; in every case, a 1.1±0.2 kb mRNA band reacted with the Clone A probe.

Figure 15:
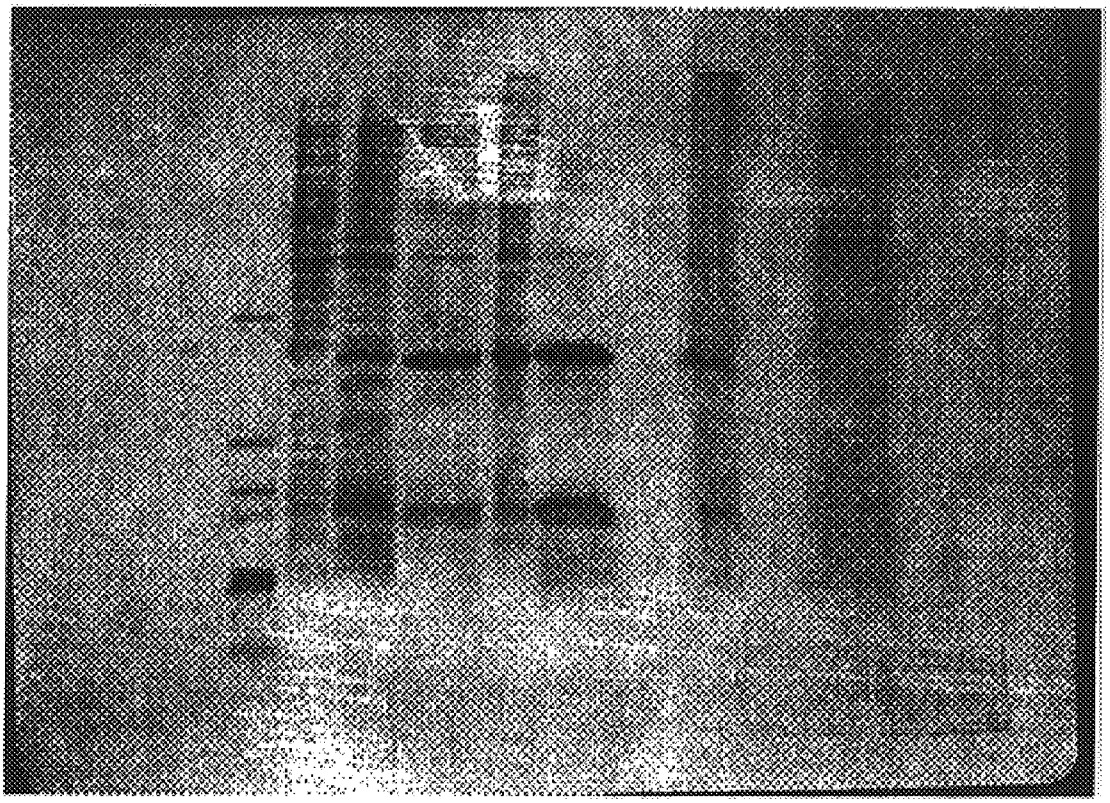
FIG. 15 is an SDS-PAGE, stained with Coomassie blue, of proteins from bacteria expressing the PET vector containing the Clone A insert. Lanes: 1—mol. wt. markers (31, 20, 17, 14, 8, 6 and 2.5 kDa); 2—$10^5$ g supernatant from uninduced bacteria; 3—$10^5$ g supernatant from IPTG induced bacteria; 4—40% $NH_3SO_4$ precipitate; 5—centricon (30 kDa) retentate; 6—centricon (10 kDa) retentate; 7—blank; 8—guanidiniumHCl treated; 9—blank; 10—40% $NH_3SO_4$ supernatant.
Figure 16:
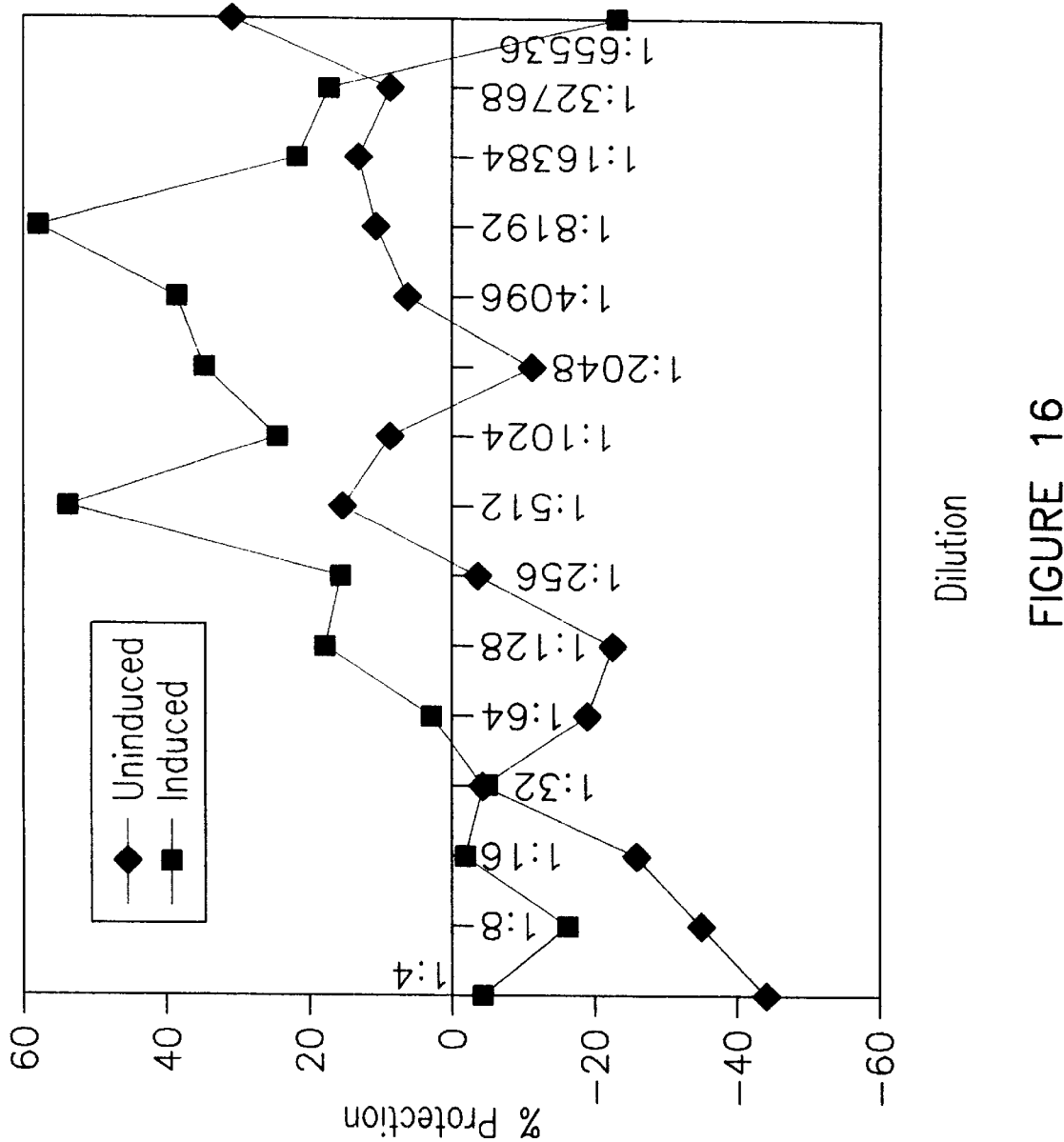
FIG. 16 is a graph showing protection of BG9 cells from TNF+CHX lysis by $10^5$ g supernatant from Clone A recombinant bacteria ($Abs_{570}$: controls~0.600; TNF+CHX~0.270).

The Clone A insert has been placed, in frame, in a pET® vector and expressed in E. coli.. The bacteria have been induced with IPTG, lysed and $10^5$xg supernatant produced. An abundant protein of the expected size for Clone A (~14 kDa) is seen on SDS-PAGE (FIG. 15) and the $10^5$xg supernatant protects against TNF-induced lysis (FIG. 16).

Figure 18:
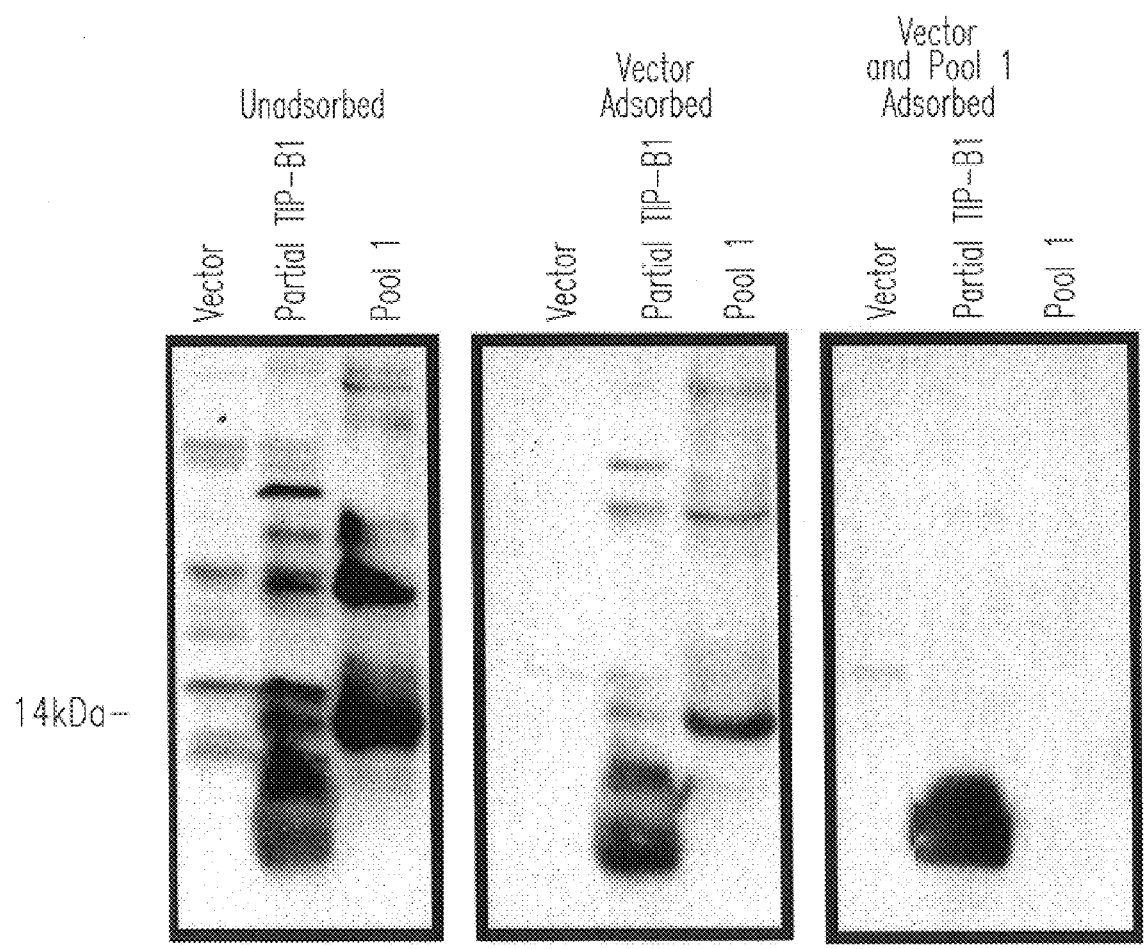
FIG. 18 shows Western blots of bacterial proteins using unadsorbed and adsorbed antiserum 459. This antiserum was generated against the recombinant partial $TIP-B_1$ protein (~14 kDa): the product of Clone A transfected bacteria.
Figure 19:
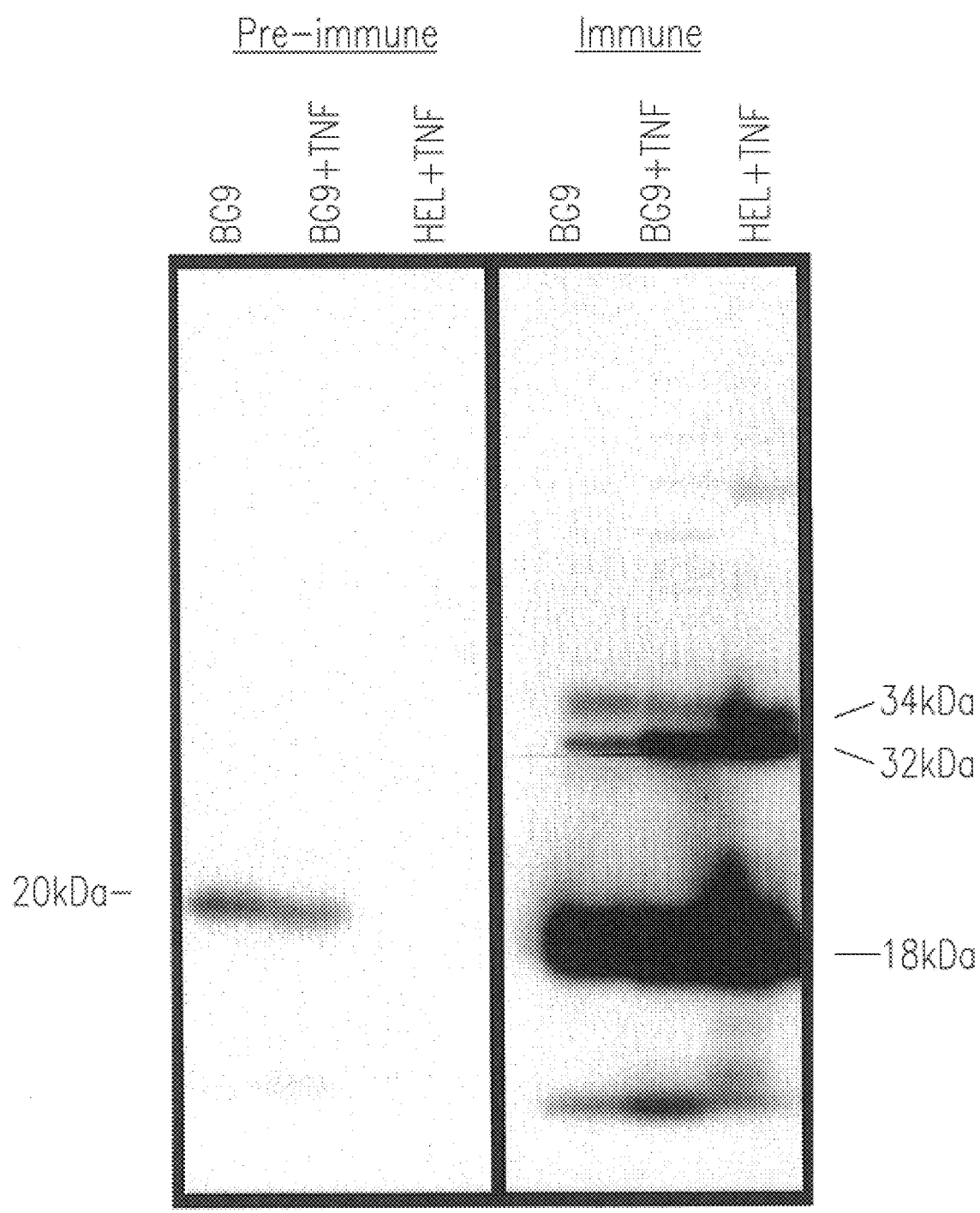
FIG. 19 shows a Western blot analysis of BG9 and HEL Cell 100 kxg supernatants with antiserum 17. This antiserum was generated against purified $TIP-B_1$ (fractions 9–11, see FIGS. 3 and 4).
Figure 20:
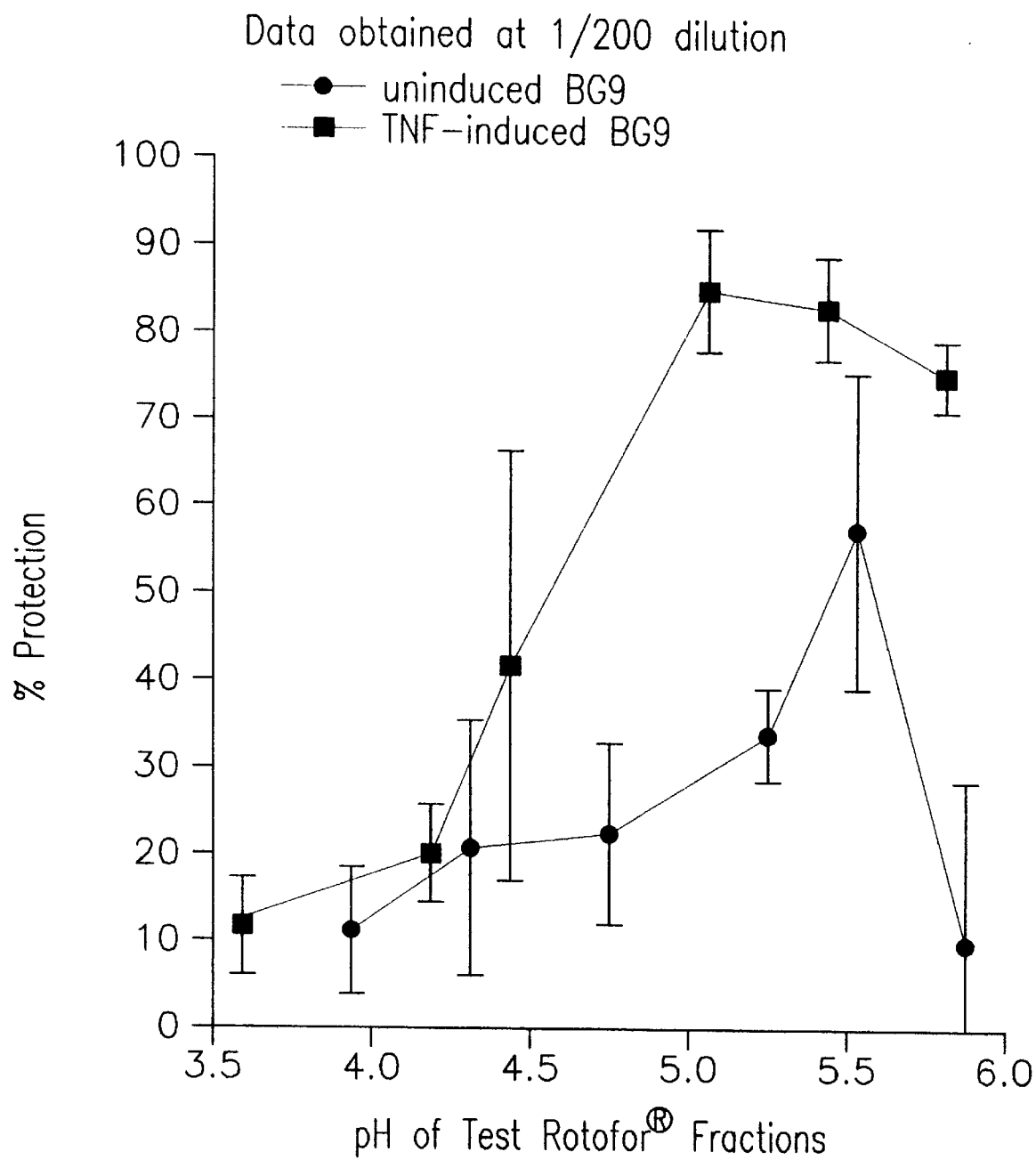
FIG. 20 is a graph showing comparison of protective activity of equal amounts of Rotofor® fractions obtained from untreated (●) and TNF-treated (■) BG9 cells.

Using purified recombinant partial TIP-B$_1$ protein, r-TIP-B1$_p$, and purified TIP-B1, polyclonal antibodies were generated in NZW rabbits. The two antisera generated, one to TIP-B$_1$ and the other to r-TIP-B$_{1p}$ were designated #17 and #459, respectively. In testing for the specificity of the antisera, antiserum 459 was found to react with some proteins present in the $10^5$xg supernatant from bacteria containing vector alone (first lane, left panel, FIG. 18) but also with a 14 kDa protein found only in the $10^5$xg supernatant of bacteria containing the vector with Clone A (tip-SN) insert (the 2nd lane, left panel) or in the pool of purified r-TIP-B$_{1p}$ used to immunize the rabbit (3rd lane, left panel). Antiserum 459 absorbed with bacteria containing vector alone no longer reacted with proteins in the $10^5$xg supernatant from bacteria containing vector alone but still reacted with proteins in two other samples (lanes 1, 2 and 3, center panel, respectively). Adsorption of the antiserum with both bacteria containing vector alone and purified r-TIP-B$_{1p}$ (pool 1) resulted in the removal of all reactivity, other than that assumed to be non-specific immunoglobulin binding to very low molecular weight material (right panel, FIG. 18). The western blots shown in FIG. 19, developed with preimmune and immune serum 17, show that the immune serum reacts specifically with proteins of approximately 18, 32 and 34 kDa in $10^5$xg supernatants from both BG9 and HEL cells. The 32 kDa protein appears to be several fold higher in the supernatant from BG9 cells treated with TNF, suggesting that it may be induced. The activity data, obtained with the Rotofor® fractions from cells with and without TNF treatment, are also consistent with the possibility of induction of the TIP-$B_1$ protein (FIG. 20). Thus, proteins from TNF treated cells found in the Rotofor® fractions in the pH range of 4.5 to 5.0 apparently had considerably more protective activity than the parallel fractions from untreated cells.

Figure 21:
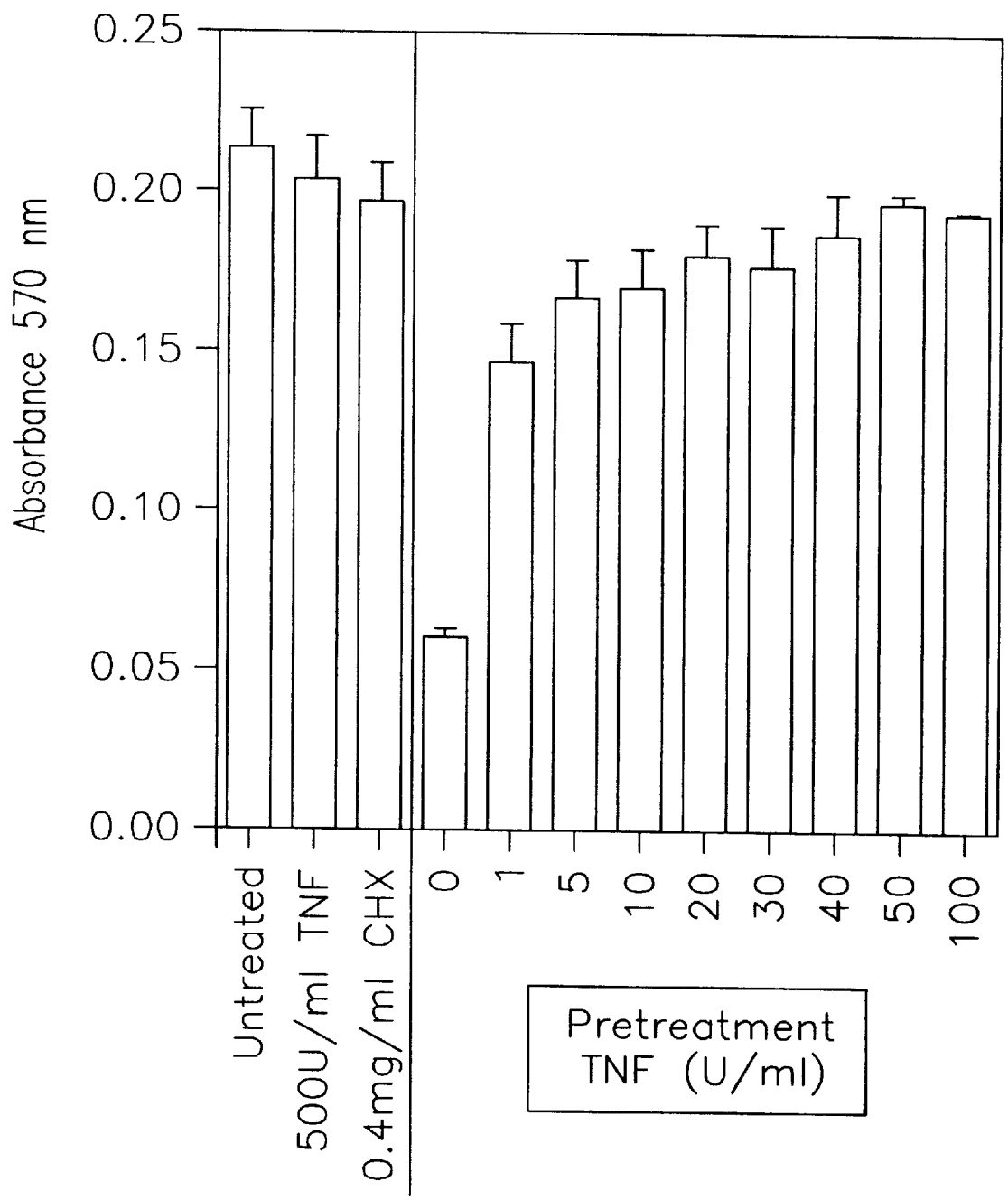
FIG. 21 is a graph showing protection of NHDF cells from TNF+CHX by pretreatment with TNF.
Figure 22:
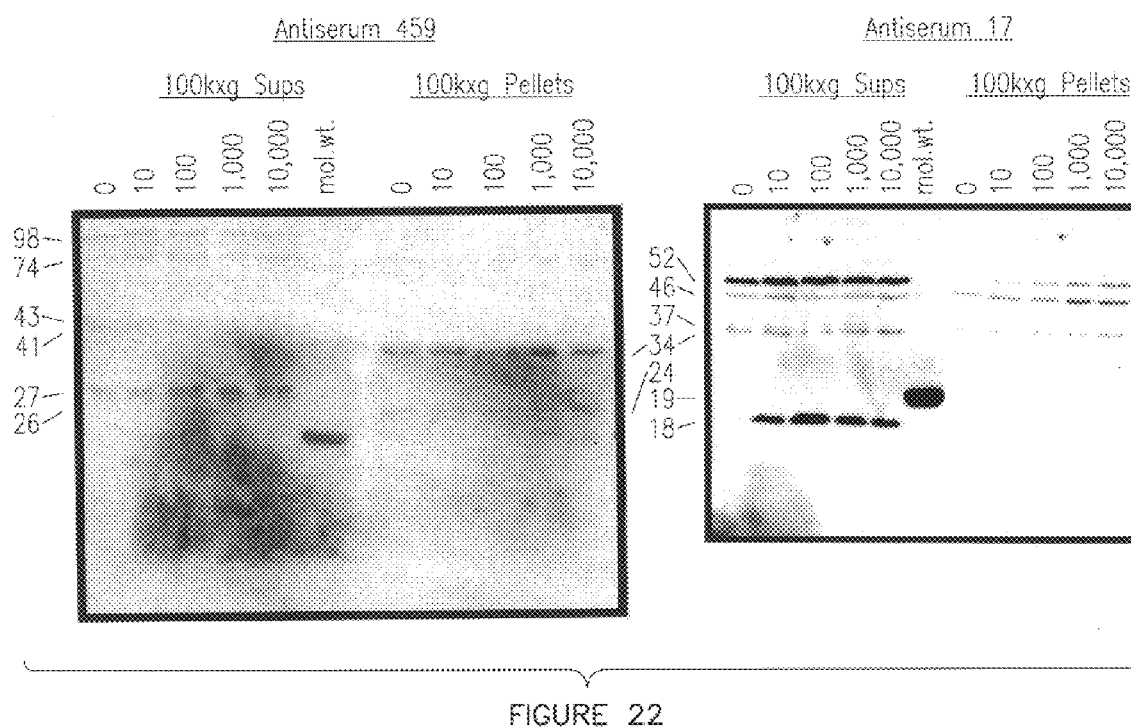
FIG. 22 is a Western blot analysis of NHDF proteins with 18 hr pre-treatment with various concentrations of TNF (U/ml) using antiserum 459 and antiserum 17.
Figure 23A:
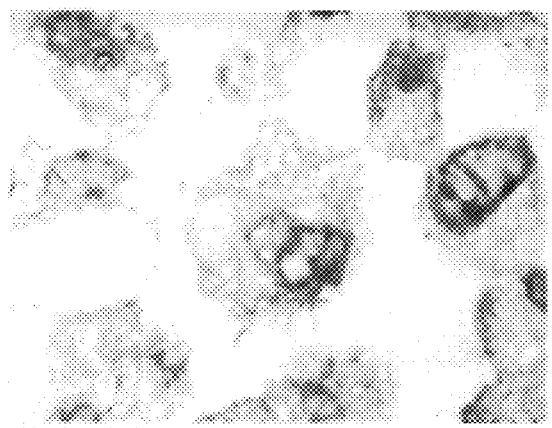
FIG. 23A is immunocytochemical analysis of paraffin embedded NHDF cells—preimmune untreated.
Figure 23B:
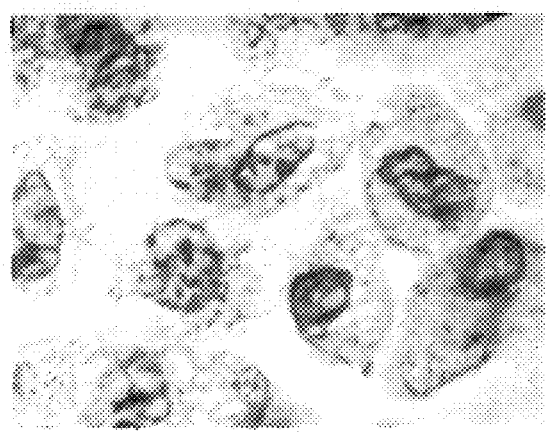
FIG. 23B is immunocytochemical analysis of paraffin embedded NHDF cells—preimmune—50 U/ml TNF 18 hours.
Figure 23C:
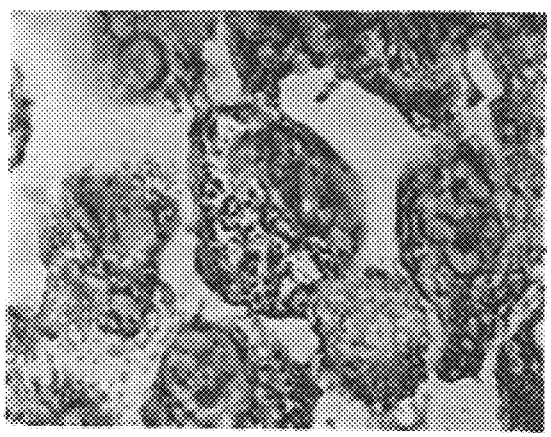
FIG. 23C is immunocytochemical analysis of paraffin embedded NHDF cells—antiserum 17 untreated.
Figure 23D:
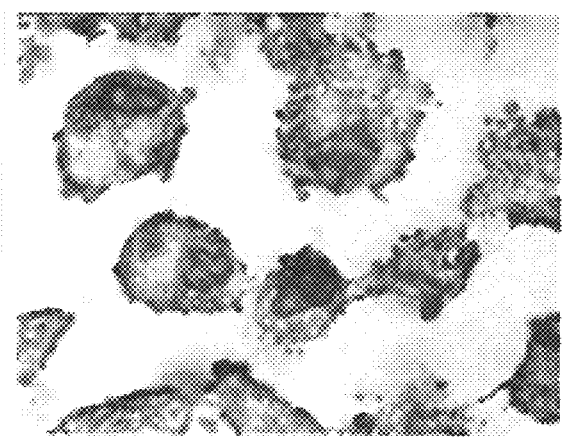
FIG. 23D is immunocytochemical analysis of paraffin embedded NHDF cells—antiserum 17—50 U/ml TNF 18 hours.
Figure 24A:
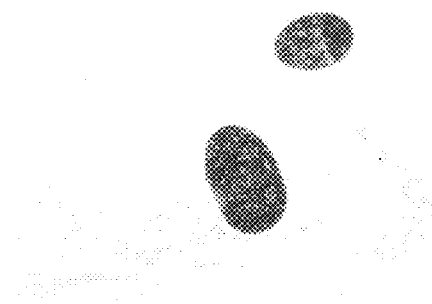
FIG. 24A is immunocytochemical analysis of NHDF cells grown on coverslips—preimmune—untreated.
Figure 24B:
FIG. 24B is immunocytochemical analysis of NHDF cells grown on coverslips—antiserum 17—untreated.
Figure 24C:
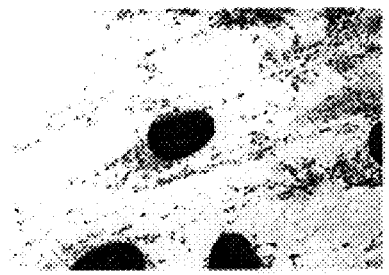
FIG. 24C is immunocytochemical analysis of NHDF cells grown on coverslips—antiserum 17—50 U/ml TNF 18 hours
Figure 28A:
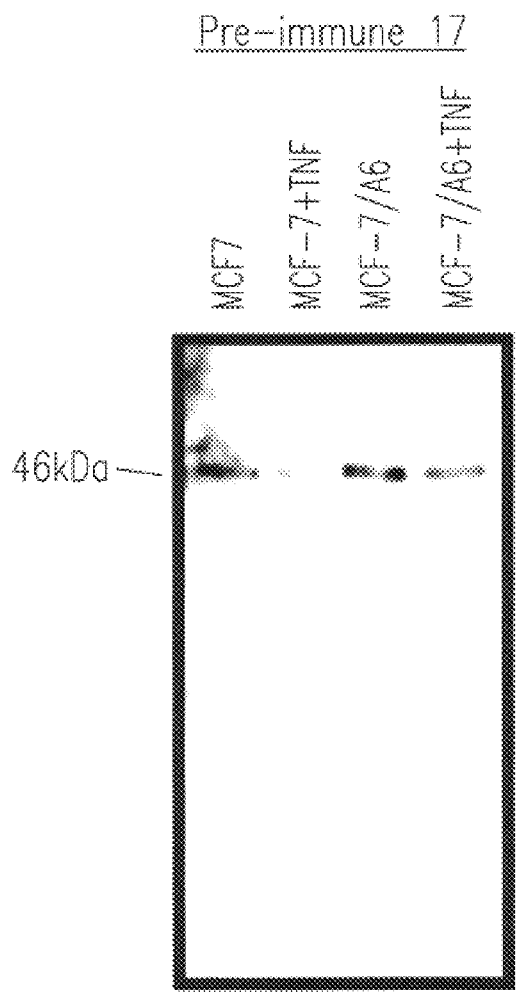
FIG. 28A is a Western blot analysis of MCF-7 and MCF-7/A6 untreated and pre-treated with 10 U/ml TNF for 18 hrs—preimmune 17.

NHDF cells had been found to have considerable message for TIP-$B_1$ (FIG. 17) and are fibroblasts as were the MLD and BG9 cells originally used as targets. Therefore, NHDF were examined for TNF plus cycloheximide sensitivity and TNF-induced protection (FIG. 21). Without pretreatment with TNF, NHDF are essentially ablated by an 18 h exposure to TNF plus CHX at the indicated concentrations. Following a 6 h pretreatment with as little as 1 U/ml TNF, however, the majority of the cells are protected. Maximal protection was achieved by pretreatment with 50 U/ml TNF. These findings suggested that NHDF might be both a suitable target cell for bioassay of TIP-$B_1$ and also a good source of TIP-$B_1$. In further investigations, NHDF cells, cultured in the presence of 0 to 10,000 U/ml TNF, were lysed and fractionated by centrifugation. The large cellular particulate fraction was removed following 12×$10^3$ xg centrifugation. The remaining material was separated at $10^5$ xg into supernatant and pellet fractions which were analyzed on parallel western blots utilizing the two antisera (FIG. 22). The patterns of reactivity seen with the two antisera are somewhat different. The 459 antiserum detected a 27 kDa protein while the 17 antiserum failed to do so. Conditions have just recently been optimized which allow for routine detection of a 27 kDa protein with the 17 antiserum. Previously, i.e. for all blots shown, the conditions used were not optimal. Antiserum 17 reacted with two proteins, a 52 and an 18 kDa, that 459 did not detect (the preimmune 17 reacts with a 46 kDa protein, see FIG. 28A, below, and therefore it is likely that this is nonspecific). Interestingly, the 18 kDa band was barely detectable in the sample not pretreated with TNF and appeared to be strongly induced. In contrast, there wasn't evidence of induction of the 52 kDa protein, but there was evidence of possible TNF-induced translocation of the protein from the cytosolic to the particulate fraction.

The possibility of translocation of antibody reactive proteins was investigated further in immunocytochemical studies (FIGS. 23A–D and 24A–C). For the analysis shown in FIGS. 23A–D, NHDF cells, with and without TNF treatment, were harvested, pelleted, formalin fixed, embedded in paraffin blocks, sectioned, counter stained with hematoxylin (blue nuclear stain), and reacted with either preimmune or antiserum 17 followed with biotinylated goat anti-rabbit antiserum and then strepavidin labeled horseradish peroxidase and substrate. For the immunocytochemical analysis shown in FIGS. 24A–C, NHDF cells grown on coverslips were either treated with TNF or not treated, air dried, frozen (−70° C.) overnight, acetone fixed, and developed as given for FIGS. 23A–D. Little or no positive reactivity was seen with the preimmune, however, considerable reactivity was seen with antiserum 17 in both experiments. In the cells which had not been treated with TNF the antiserum reactive proteins appeared to be diffusely dispersed in the cytoplasm. In contrast, in cells treated with TNF, the antiserum reactive proteins were found to be localized to distinct areas, particularly near the plasma membrane as well as perinuclear.

These findings support a possible translocation step for TIP-$B_1$ in the induction of protection seen following exposure to low concentrations of TNF.

Figure 25A:
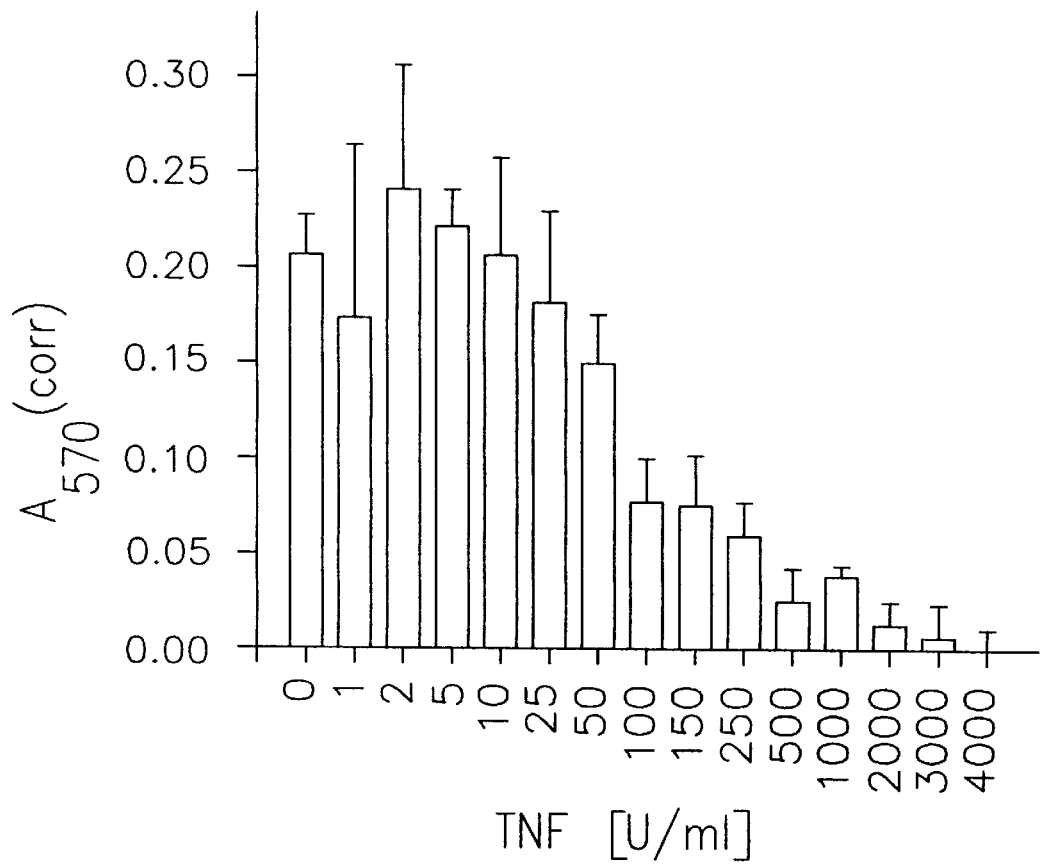
FIG. 25A is a graph showing that MCF7 cells are lysed by TNF (72 h, with MTT added for the last 6 h).
Figure 25B:
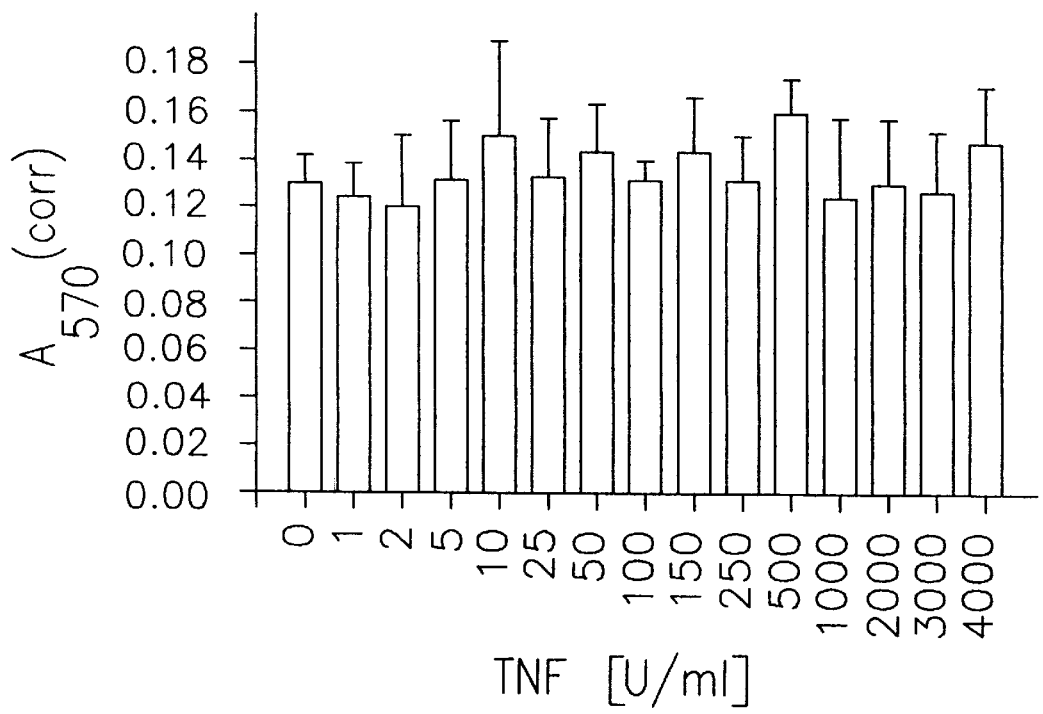
FIG. 25B is a graph showing that the MDR subline MCF7/A6 are TNF resistant (72 h, with MTT added for the last 6 h).
Figure 26:
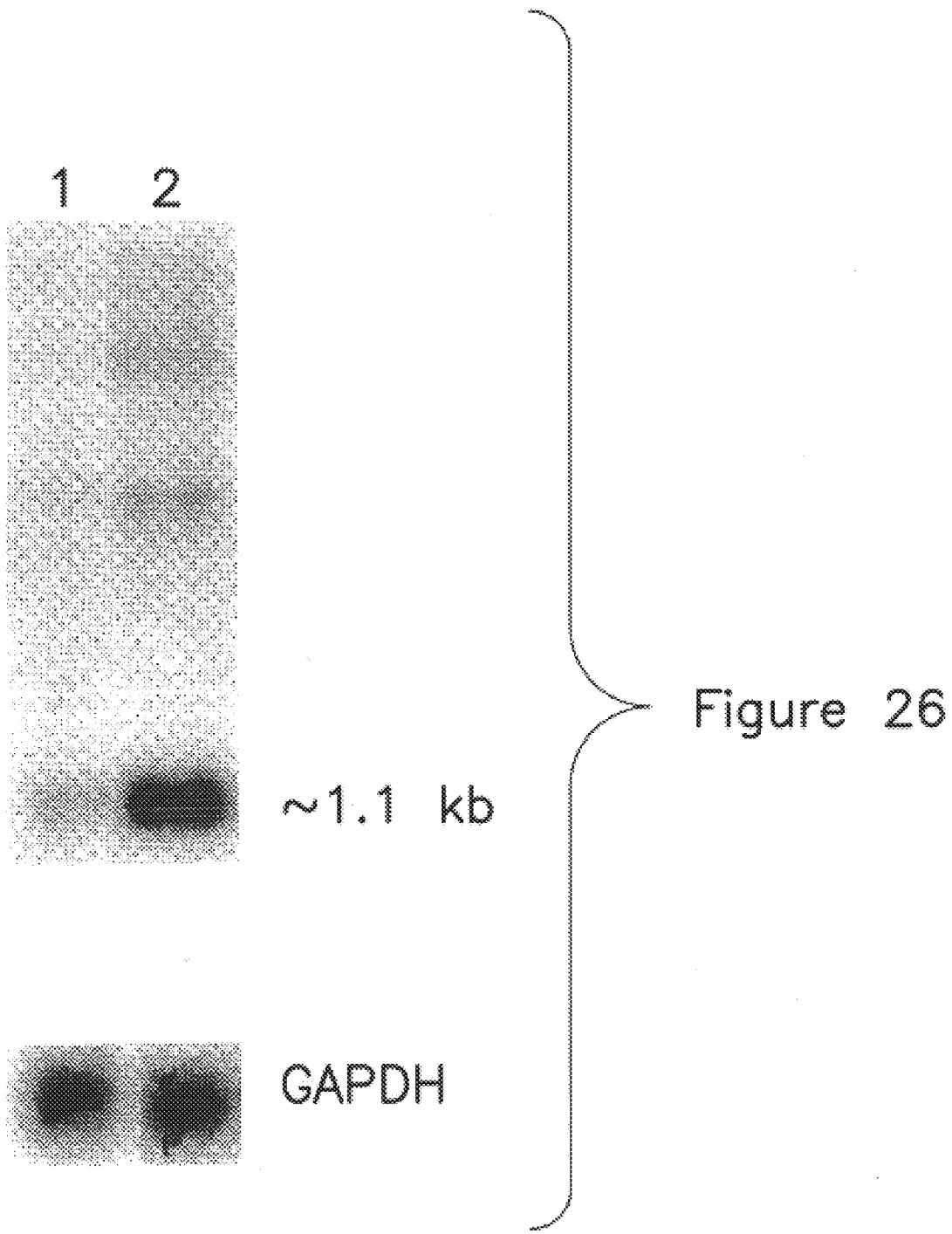
FIG. 26 is a gel showing that MCF7/A6 cells (lane 2) contain twice as much $TIP-B_1$ mRNA as MCF7 (lane 1) cells.
Figures 27A, 27B:
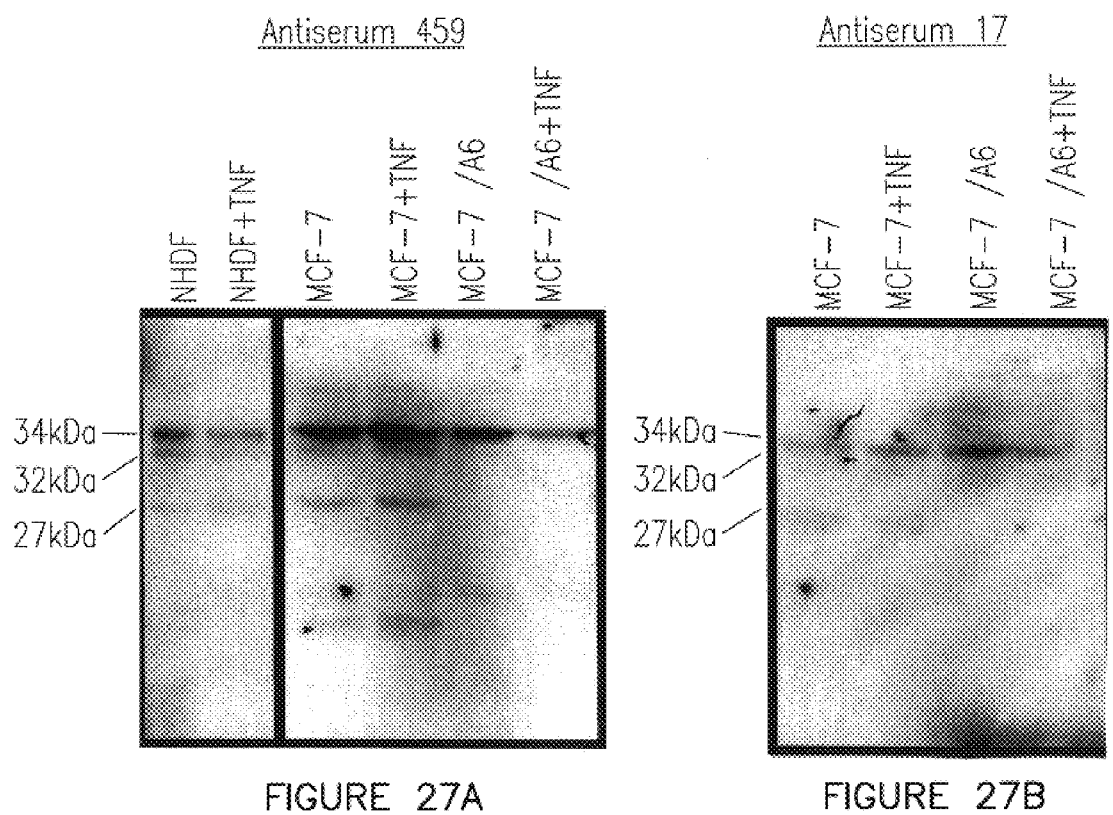
FIG. 27A is a Western blot analysis of selected cell lines cell proteins with or without 18 hr 10 U/ml TNF pre-treatment—antiserum 459.
FIG. 27B is a Western blot analysis of selected cell lines cell proteins with or without 18 hr 10 U/ml TNF pre-treatment—antiserum 17.
Figure 28B:
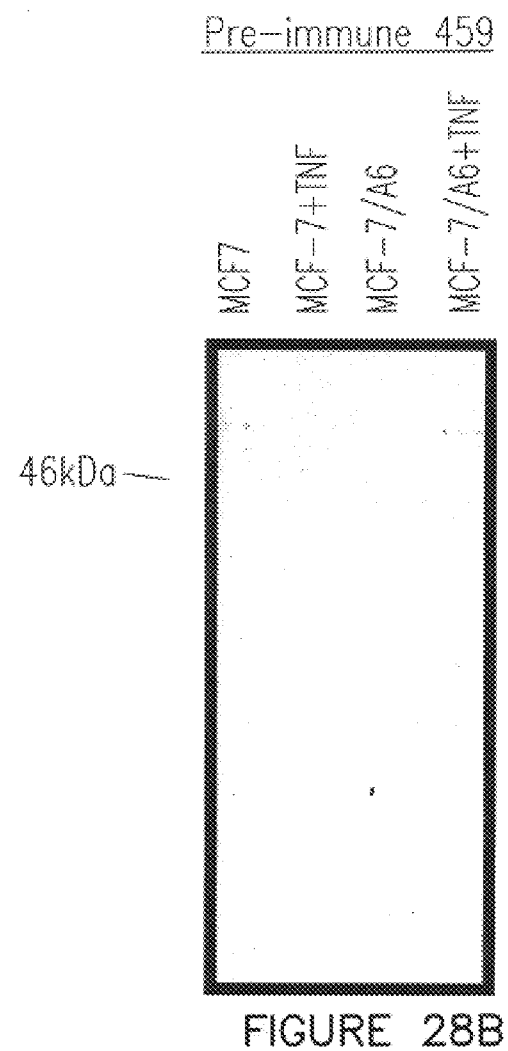
FIG. 28B is a Western blot analysis of MCF-7 and MCF-7/A6 untreated and pre-treated with 10 U/ml TNF for 18 hrs—preimmune 459.
Figure 29:
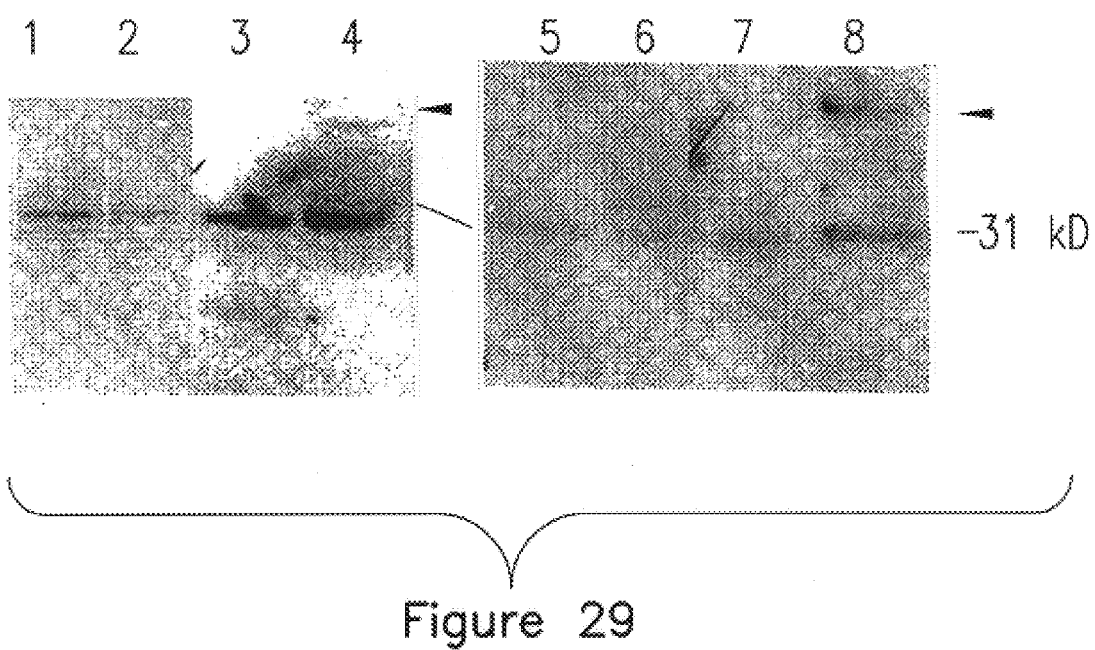
FIG. 29 are gels showing anti-$TIP-B_1$ (#17) and anti-r-$TIP-B_{1P}$ (#459) antersera have similar reactivities and two different drug resistant cell sublines express an ~60 kDa ◂ protein which reacts with antiserum 17. Proteins were from MCF7 (lanes 1,2); MCF7/A6 (lanes 3,4); REH (lanes 5,6); REH3.6 (lanes 7,8). Antisera used were #459 (lanes 1,3,5,7) and #17 (lanes 2,4,6,8).

The MCF7 cell line, human breast adenocarcinoma, was found to be sensitive to TNF but its MDR variant, MCF7/A6, was not (FIGS. 25A and 25B). MCF7/A6 cells contain twice as much TIP-$B_1$ mRNA as MCF7 cells (FIG. 26). Based upon these results, western blots assessing $10^5$xg supernatants from nontreated and TNF treated cells were carried out using NHDF as a positive control (FIGS. 27A and 27B, see FIGS. 28A and 28B for results with preimmune sera). A 27 kDa protein was detected in the MCF7 but not the MCF7/A6 supernatants. A 34 kDa protein was detected in both, but its TNF-inducibility appeared to be different between the two cell lines. Finally, using the acute lymphoblastic leukemia REH and an ~8-fold resistant variant, REH3.6, developed in our laboratory, it was found that the two antisera detected similar proteins in the two parent/MDR pairs (FIG. 29). Antiserum 17 also detected a higher molecular weight protein which was seen in the MDR variants but not in the parental wild type.

SEQUENCE LISTING

```
<160> NUMBER OF SEQ ID NOS: 7

<210> SEQ ID NO 1
<211> LENGTH: 10
<212> TYPE: PRT
<213> ORGANISM: HOMO SAPIENS
<220> FEATURE:
<221> NAME/KEY: UNSURE
<222> LOCATION: 3,6,8
<223> OTHER INFORMATION: Xaa at position 3 is either E or L.  Xaa at
      position 6 is either P or D.  Xaa at position 8 can be any amino
      acid.  Xaa residues at positions 3,6, and 8, in conjunction with
      the remainder of the sequence is the amino terminus of a protein
      which inhibits TNF-induced cytotoxicity

<400> SEQUENCE: 1

Val Val Xaa Ala Val Xaa Leu Xaa Ala His
```

```
1               5                    10
```

```
<210> SEQ ID NO 2
<211> LENGTH: 18
<212> TYPE: PRT
<213> ORGANISM: HOMO SAPIENS
<220> FEATURE:
<221> NAME/KEY: UNSURE
<222> LOCATION: 14
<223> OTHER INFORMATION: Xaa residues at position 14 can be any amino
      acid and in conjunction with the remainder of the sequence is the
      amino terminus of a protein which inhibits TNF-induced
      cytotoxicity. This sequence is homologous to the amino terminal
      sequence of two other known proteins: GST(pi)and FAEESIII

<400> SEQUENCE: 2

Ala Pro Tyr Thr Val Val Tyr Phe Pro Val Arg Gly Arg Xaa Ala Ala
1               5                   10                  15

Leu Arg

<210> SEQ ID NO 3
<211> LENGTH: 13
<212> TYPE: PRT
<213> ORGANISM: HOMO SAPIENS

<400> SEQUENCE: 3

Ser Gln Gln Ser Glu Val Thr Arg Ile Leu Asp Gly Lys
1               5                   10

<210> SEQ ID NO 4
<211> LENGTH: 27
<212> TYPE: PRT
<213> ORGANISM: HOMO SAPIENS
<220> FEATURE:
<221> NAME/KEY: UNSURE
<222> LOCATION: 1
<223> OTHER INFORMATION: The Xaa residue at position 1 can be any amino
      acid and in conjunction with the remainder of the sequence in the
      peptide is a sequence derived from internal peptides of TIP-B1, a
      protein which inhibits TNF-induced cyto-toxicity and apoptosis

<400> SEQUENCE: 4

Xaa Ile Gln Tyr Gln Leu Val Asp Ile Ser Gln Asp Asn Ala Leu Arg
1               5                   10                  15

Asp Glu Met Arg Ala Leu Ala Gly Asn Pro Lys
                20                  25

<210> SEQ ID NO 5
<211> LENGTH: 12
<212> TYPE: PRT
<213> ORGANISM: HOMO SAPIENS
<220> FEATURE:
<221> NAME/KEY: UNSURE
<222> LOCATION: 1
<223> OTHER INFORMATION: The Xaa residue at position 1 can be any amino
      acid and in conjunction with the remainder of the sequence in the
      peptide is a sequence derived from internal peptides of TIP-B1, a
      protein which inhibits TNF-induced cyto-toxicity and apoptosis

<400> SEQUENCE: 5

Xaa Thr Pro Pro Gln Ile Val Asn Gly Asp Gln Tyr
1               5                   10

<210> SEQ ID NO 6
<211> LENGTH: 783
<212> TYPE: DNA
<213> ORGANISM: HOMO SAPIENS
<220> FEATURE:
```

```
<223> OTHER INFORMATION: This sequence encodes the TIP-B1 peptides of
      SEQ. ID. #3, SEQ. ID. #4 and SEQ. ID. #5

<400> SEQUENCE: 6
ggcacgagca cggcggcggc gtcgtctccc ggcagtgcag ctgccgctac cgccgccctc      60
tgcccgccgg cccgtctgtc taccccagc atgagcggcc tgcgcgtcta cagcacgtcg     120
gtcaccggct cccgcgaaat caagtcccag cagagcgagg tgacccgaat cctggatggg    180
aagcgcatcc aataccagct agtggacatc tcccaggaca acgccctgag ggatgagatg    240
cgagccttgg caggcaaccc caaggccacc ccacccagag ttgtcaacgg ggaccagtac    300
tgtggggact atgagctctt cgtggaggct gtggaacaaa acacgctgca ggagttcctg    360
aagctggctt gagtcaagcc tgtccagagt tccctgctg gactccatca ccacactccc     420
cccagccttc acctggccat gaaggaccttt ttgaccaact ccctgtcatt cctaacctaa   480
ccttagagtc cctcccccaa tgcaggccac ttctcctccc tcctctctaa atgtagtccc    540
ctctcctcca tctaaaggca acattcctta cccattagtc tcagaaattg tcttaagcaa    600 cagcccaaa tgctggctgc cccagccaa gcattgggc cgccatcctg cctggcactg       660
gctgatgggc acctctgttg gttccatcag ccagagctcg ccaaaggccc cgcagtccct    720
ctcccaggag gaccctagag gcaattaaat gatgtcctgt tccattgaaa aaaaaaaaa    780 aaa                                                                  783

<210> SEQ ID NO 7
<211> LENGTH: 123
<212> TYPE: PRT
<213> ORGANISM: HOMO SAPIENS
<220> FEATURE:
<223> OTHER INFORMATION: This is the amino acid sequence predicted from
      translation of the DNA sequence 4 (=clone A=rtip-b1p cDNA) and
      which contains the TIP-B1 peptides of SEQ. ID. #3, 4, AND 5

<400> SEQUENCE: 7

Gly Thr Ser Thr Ala Ala Ala Ser Ser Pro Gly Ser Ala Ala Ala Ala
 1               5                  10                  15

Thr Ala Ala Leu Cys Pro Pro Ala Arg Leu Ser Thr Pro Ser Met Ser
             20                  25                  30

Gly Leu Arg Val Tyr Ser Thr Ser Val Thr Gly Ser Arg Glu Ile Lys
         35                  40                  45

Ser Gln Gln Ser Glu Val Thr Arg Ile Leu Asp Gly Lys Arg Ile Gln
     50                  55                  60

Tyr Gln Leu Val Asp Ile Ser Gln Asp Asn Ala Leu Arg Asp Glu Met
 65                  70                  75                  80

Arg Ala Leu Ala Gly Asn Pro Lys Ala Thr Pro Pro Gln Ile Val Asn
                 85                  90                  95

Gly Asp Gln Tyr Cys Gly Asp Tyr Glu Leu Phe Val Glu Ala Val Glu
            100                 105                 110

Gln Asn Thr Leu Gln Glu Phe Leu Lys Leu Ala
            115                 120
```

What is claimed is:

1. A protein designated Tumor Necrosis Factor Inhibitory Protein-$B_1$ TIP-$B_1$) purified to homogeneity, said protein having a molecular weight of about 27 kD and being capable of inhibiting the action of TNF upon a cell when said protein is introduced into extracellular medium surrounding the cell, and said protein being free of sequences which interfere with normal cellular TNF binding sites and being free of sequences which directly bind to TNF, said protein have a terminal amino acid sequence of A-P-Y-T-V-V-Y-F-P-V-R-G-R-X-A-A-L-R.

2. The protein of claim 1 wherein said protein has the 52 amino acid internal peptide sequence SQQSEVTRILDGK (SEQ. ID. #3), XIQYQLVDISQ DNALRDEMRALAG-NPK (SEQ. ID. #4), XTPPQIVNGDQY (SEQ. ID. #5).

3. A method for inhibiting the action of TNF upon a cell which comprises exposing the cell to an effective amount of the TIP-$B_1$ protein of claim 2 to inhibit the action of TNF upon a cell.

4. A method for inhibiting the action of TNF upon a cell which comprises exposing the cell to an effective amount of the TIP-$B_1$ protein of claim 1 to inhibit the action of TNF upon a cell.

* * * * *

UNITED STATES PATENT AND TRADEMARK OFFICE
CERTIFICATE OF CORRECTION

PATENT NO. : 6,197,744 B1
DATED : March 6, 2001
INVENTOR(S) : Erica Berleth et al.

It is certified that error appears in the above-identified patent and that said Letters Patent is hereby corrected as shown below:

Claim 1,
Line 2, please place a beginning parenthesis before "TIP-$B_1$)".

Signed and Sealed this

Twenty-fifth Day of December, 2001

Attest:

Attesting Officer

JAMES E. ROGAN
Director of the United States Patent and Trademark Office